United States Patent
Friend et al.

(10) Patent No.: US 7,819,976 B2
(45) Date of Patent: *Oct. 26, 2010

(54) BIOMASS TREATMENT METHOD

(75) Inventors: Julie Friend, Claymont, DE (US); Richard T. Elander, Evergreen, CO (US); Melvin P. Tucker, III, Lakewood, CO (US); Robert C. Lyons, Arvada, CO (US)

(73) Assignees: E. I. du Pont de Nemours and Company, Wilmington, DE (US); Alliance For Sustainable Energy LLC, Golden, CO (US)

( * ) Notice: Subject to any disclaimer, the term of this patent is extended or adjusted under 35 U.S.C. 154(b) by 591 days.

This patent is subject to a terminal disclaimer.

(21) Appl. No.: 11/843,142

(22) Filed: Aug. 22, 2007

(65) Prior Publication Data

US 2009/0050134 A1  Feb. 26, 2009

(51) Int. Cl.
*C13K 1/02* (2006.01)
(52) U.S. Cl. .................. 127/1; 127/36; 127/37
(58) Field of Classification Search .............. 127/1, 127/36, 37
See application file for complete search history.

(56) References Cited

U.S. PATENT DOCUMENTS

| | | | |
|---|---|---|---|
| 3,565,687 A * | 2/1971 | Suminoe et al. ............. 127/37 |
| 4,136,207 A | 1/1979 | Bender | |
| 4,186,658 A | 2/1980 | Brown | |
| 4,461,648 A | 7/1984 | Foody | |
| 4,859,283 A | 8/1989 | Jayawant | |
| 5,008,473 A | 4/1991 | Breitkopf et al. | |
| 5,037,663 A | 8/1991 | Dale | |
| 5,171,592 A * | 12/1992 | Holtzapple et al. ........... 426/69 |
| 5,192,673 A | 3/1993 | Jain et al. | |
| 5,356,812 A | 10/1994 | Matsuyama et al. | |
| 6,013,494 A | 1/2000 | Nakamura et al. | |
| 6,106,888 A | 8/2000 | Dale et al. | |
| 6,159,738 A | 12/2000 | Donnelly et al. | |
| 6,176,176 B1 | 1/2001 | Dale et al. | |
| 6,228,630 B1 | 5/2001 | Kofod et al. | |
| 6,358,717 B1 | 3/2002 | Blaschek et al. | |
| 6,416,621 B1 * | 7/2002 | Karstens ..................... 162/22 |
| 6,514,733 B1 | 2/2003 | Emptage et al. | |
| 6,777,207 B2 | 8/2004 | Kjeldsen et al. | |
| 6,861,237 B2 | 3/2005 | Anderson et al. | |
| 6,962,805 B2 | 11/2005 | Asakura et al. | |
| 2003/0162271 A1 | 8/2003 | Zhang et al. | |

(Continued)

FOREIGN PATENT DOCUMENTS

EP   0 263 515 A2   4/1988

(Continued)

OTHER PUBLICATIONS

Iyer et al, "Ammonia Recycled Percolation Process for Pretreatment of Herbaceous Biomass", Humana Press Inc., (1996), pp. 121-132.*

(Continued)

*Primary Examiner*—David M Brunsman

(57) ABSTRACT

A method for treating biomass was developed that uses an apparatus which moves a biomass and dilute aqueous ammonia mixture through reaction chambers without compaction. The apparatus moves the biomass using a non-compressing piston. The resulting treated biomass is saccharified to produce fermentable sugars.

19 Claims, 6 Drawing Sheets

U.S. PATENT DOCUMENTS

| | | | |
|---|---|---|---|
| 2003/0170834 | A1 | 9/2003 | Gatenby et al. |
| 2005/0250192 | A1 | 11/2005 | Shanmugam et al. |
| 2006/0003429 | A1 | 1/2006 | Frost et al. |
| 2009/0221042 | A1* | 9/2009 | Dale et al. ................. 435/105 |

FOREIGN PATENT DOCUMENTS

| | | |
|---|---|---|
| EP | 0 332 234 A2 | 9/1989 |
| EP | 136 359 B1 | 4/1991 |
| JP | 47004505 | 3/1972 |
| JP | 47038995 | 10/1972 |
| JP | 51006237 | 1/1976 |
| JP | 51019037 | 2/1976 |
| JP | 54032070 | 3/1979 |
| JP | 54037235 | 3/1979 |
| JP | 56008596 | 1/1981 |
| JP | 56010035 | 2/1981 |
| JP | 57150381 | 9/1982 |
| WO | WO 2007/041269 A2 | 4/2007 |
| WO | WO 2007/050671 A2 | 5/2007 |

OTHER PUBLICATIONS

Waiss et al, "Improving Digestibility of Straws for Ruminant Feed by Aqueous Ammonia", Journal of Animal Science, vol. 35, No. 1, (1972), pp. 109-112.*
U.S. Appl. No. 11/402,757, filed Apr. 12, 2006, James B. Dunson et al.
U.S. Appl. No. 11/741,892, filed Apr. 30, 2007, Gail K. Donaldson et al.
U.S. Appl. No. 11/741,916, filed Apr. 30, 2007, Gail K. Donaldson et al.
U.S. Appl. No. 60/847,813, filed Sep. 28, 2006, Paul V. Vitanen et al.
U.S. Appl. No. 60/847,856, filed Sep. 28, 2006, Paul V. Vitanen et al.
U.S. Appl. No. 11/402,464, filed Apr. 12, 2006, James B. Dunson, Jr. et al.
U.S. Appl. No. 11/403,087, filed Apr. 12, 2006, James B. Dunson, Jr. et al.
Lynd et al., Microbial Cellulose Utilization: Fundamentals and Biotechnology, Microbiol. Mol. Biol. Rev., 2002, vol. 66:506-577.
Eur. J. Biochem., Nomenclature Committee of the International Union of Biochemistry and Molecular Biology, Supplement: Corrections and Additions, 1994, vol. 223:1-5.
Eur J. Biochem., Nomenclature Committee of the International Union of Biochemistry and Molecular Biology, Supplement 2: Corrections and Additions, 1995, vol. 232:1-6.
Eur J. Biochem., Nomenclature Committee of the International Union of Biochemistry and Molecular Biology, Supplement 3: Corrections and Additions, 1996, vol. 237:1-5.
Eur J. Biochem., Nomenclature Committee of the International Union of Biochemistry and Molecular Biology, Supplement 4: Corrections and Additions, 1997, vol. 250:1-6.
Eur. J. Biochem., Nomenclature Committee of the International Union of Biochemistry and Molecular Biology, Enzyme Supplement 5, 1999, vol. 264:610-650.
Miller, Use of Dinitrosalicylic Acid Reagent for Determination of Reducing Sugar, Anal. Chem., 1959, vol. 31:426-428.
Jones et al., Acetone-Butanol Fermentation Revisited, Microbiol. Rev., 1986, vol. 50:484-524.
Underwood et al., Genetic Changes to Optimize Carbon Partitioning Between Ethanol and Biosynthesis in Ethanologenic *Escherichia coli,* Appl. Environ. Microbiol., 2002, vol. 68:6263-6272.
Zhou et al., Production of Optically Pure D-Lactic Acid in Mineral Salts Medium by Metabolically Engineered *Escherichia coli,* Applied and Environ. Microbiology, 2003, vol. 69:399-407.
Tay et al., Production of L (+)-Lactic Acid From Glucose and Starch by Immobilized Cells of *Rhizopus oryzae* in a Rotating Fibrous Bed Bioreactor, Biotechnol. Bioeng., 2002, vol. 80:1-12.

Niu et al., Benzene-Free Synthesis of Adipic Acid, Biotechnol. Prog., 2002, vol. 18:201-211.
Cheryan et al., Production of Acetic Acid by *Clostridium thermoaceticum,* Adv. Appl. Microbiol., 1997, vol. 43:1-33.
Freer, Acetic Acid Production by Dekkera/Brettanomyces Yeasts, World J. Microbiol. Biotechnol., 2002, vol. 18:271-275.
Lin et al., Metabolic Engineering of Aerobic Succinate Systems in *Escherichia coli* to Improve Process Productivity and Achieve the Maximum Theoretical Succinate Yield, Eng., 2005, vol. 7:116-127.
Li et al., Efficient Pyruvate Production by a Multi-Vitamin Auxotroph of *Torulopsis glabrata:* Key Role and Optimization of Vitamin Levels, Appl. Microbiol. Technol., 2001, vol. 55:680-685.
Yokota et al., Pyruvic Acid Production by an F-Atpase Defective Mutant of *Escherichia coli* W1485LIP2, Biosci. Biotech. Biochem., 1994, vol. 58:2164-2167.
Suwannakham et al., Enhanced Propionic Acid Fermentation by *Propionibacterium acidipropionic* Mutant Obtained by Adaptation in a Fibrous-Bed Bioreactor, Biotechnol. Bioeng., 2005, vol. 91:325-337.
Wu et al., Extractive Fermentation for Butyric Acid Production From Glucose by *Clostridium tyrobutyricum,* Biotechnol. Bioeng., 2003, vol. 82:93-102.
Anantassiadis et al., Process Optimization of Continuous Gluconic Acid Fermentation by Isolated Yeast-Like Strains of *Aureobasidium pullulans,* Biotechnol. Bioeng., 2005, vol. 91:494-501.
Singh et al., Optimisation of Fermentation Conditions for Gluconic Acid Production by a Mutant of *Aspergillus niger,* Indian J. Exp. Biol., 2001, vol. 39:1136-1143.
Elfari et al., A Gluconobacter Oxydans Mutant Converting Glucose Almost Quantitatively to 5-Keto-D-Gluconic Acid, Appl. Microbiol. Biotech., 2005, vol. 66:668-674.
Reddy et al., Enhanced Production of Itaconic Acid From Corn Starch and Market Refuse Fruits by Genetically Manipulated *Aspergillus terreus* SKR10, Bioresour. Technol., 2002, vol. 85:69-71.
Ui-Haq et al., Optimization of Nitrogen for Enhanced Citric Acid Productivity by a 2-Deoxy D-Glucose Resistant Culture of *Aspergillus niger* NG-280 Bioresour. Technol., 2005, vol. 96:645-648.
Mussatto et al., Xylitol Production From High Xylose Concentration: Evaluation of the Fermentation in Bioreactor Under Different Stirring Rates, J. of Appl. Microbiol., 2003, vol. 95:331-337.
Gorenflo et al., Development of a Process for the Biotechnological Large-Scale Production of 4-Hydroxyvalerate-Containing Polyesters and Characterization of Their Physical and Mechanical Properties, Biomacromolecules, 2001, vol. 2:45-57.
Ui et al., Production of L-2,3-Butanediol by a New Pathway Constructed in *Escherichia coli,* Lett. Appl. Microbiol., 2004, vol. 39:533-537.
Nakayama et al., Fermentative Production of L-Arginine, Arg. Biol. Chem., 1972, vol. 36:1675-1684.
Groot et al., Technologies for Butanol Recovery Intergrated With Fermentations, Process Biochem., 1992, vol. 27:61-75.
Okamoto et al., Development of an Industrially Stable Process for L-Threonine Fermentation by an L-Methionine-Auxotrophic Mutant of *Escherichia coli,* J. Biosci. Bioeng., 2000, vol. 89:79-87.
Kumar et al., Effect of Cysteine on Methionine by a Regulatory Mutant of *Corynebacterium lilium,* Bioresour. Technol., 2005, vol. 96:287-294.
Durre, Appl. New Insights and Novel Developments in Clostridial Acetone/Butanol/Isopropanol Fermentation, Microbiol. Biotechnol., 1998, vol. 49:639-648.
Janssen, Propanol as an End Product of Threonine Fermentation, Arch. Microbiol., 2004, vol. 182:482-486.
Yamadaya et al., Hydrocracking of Tetralin on Supported Nickel-Tungsten Catalysts, Bullentin of the Chemical Society of Japan, 1977, vol. 50:79-87.
A.C. Waiss et al., Improving Digestibility of Straws for Ruminant Feed by Aqueous Ammonia, Journal of Animal Science, 1972, vol. 35:109-112.
International Search Report of related PCT/US2008/073418 mailed Jun. 25, 2009.

* cited by examiner

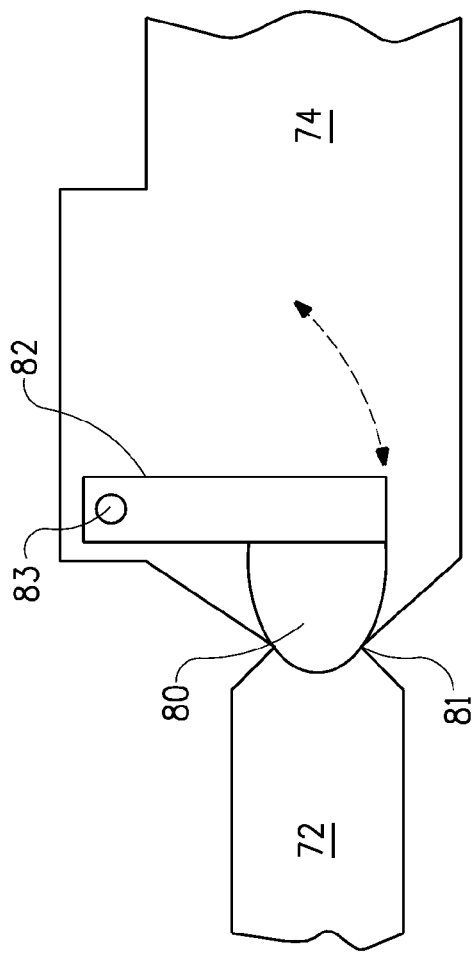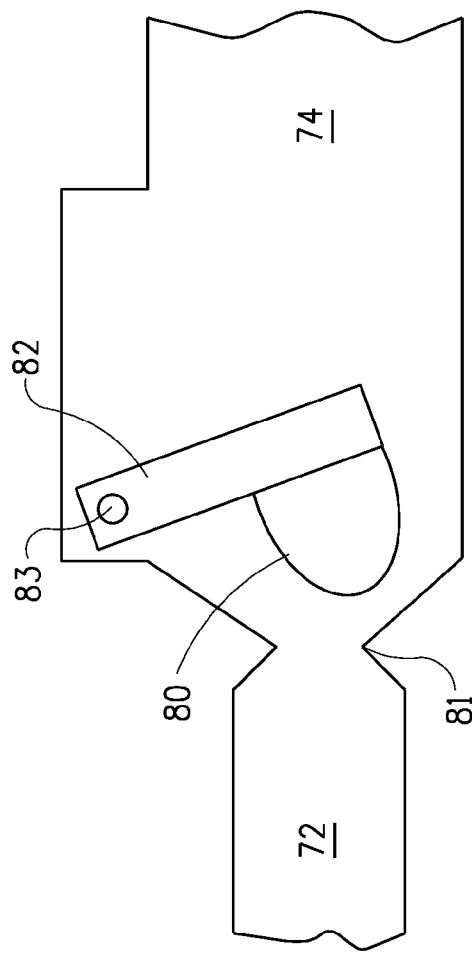
FIG. 6A
FIG. 6B

BIOMASS TREATMENT METHOD

STATEMENT OF GOVERNMENT RIGHTS

This invention was made with United States Government support under Contract Nos. 04-03-CA-70224 and DE-FC36-03GO13146 awarded by the Department of Energy. The government has certain rights in this invention.

FIELD OF THE INVENTION

A method for treatment of biomass that includes a specified apparatus is provided. The method using the apparatus moves biomass into and through a reactor in a non-compacted state, where a treatment method of impregnating and reacting biomass with dilute aqueous ammonia at moderate temperature and pressure is performed.

BACKGROUND

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as fuels and other chemicals. Cellulosic and lignocellulosic feedstocks and wastes, composed of carbohydrate polymers comprising cellulose, hemicellulose, glucans and lignin are generally treated by a variety of chemical, mechanical and enzymatic means to release primarily hexose and pentose sugars, which can then be fermented to useful products.

First, biomass feedstocks are treated to make the carbohydrate polymers of cellulosic and lignocellulosic materials more readily available to saccharification enzymes, which is often called pretreatment. The pretreated biomass is then further hydrolyzed in the presence of saccharification enzymes to release oligosaccharides and/or monosaccharides in a hydrolysate. Saccharification enzymes used to produce fermentable sugars from pretreated biomass typically include one or more glycosidases, such as cellulose-hydrolyzing glycosidases, hemicellulose-hydrolyzing glycosidases, and starch-hydrolyzing glycosidases, as well as peptidases, lipases, ligninases and/or feruloyl esterases. Saccharification enzymes and methods for biomass treatment are reviewed in Lynd, L. R., et al. (Microbiol. Mol. Biol. Rev. (2002) 66:506-577).

It is desirable to have a system and/or method for treating biomass that is effective and economical for use on a large scale. Treatment of biomass as a concentrated, high dry weight material is needed to produce the high concentrations of fermentable sugars needed for fermentation to products economically. Thus movement of material including a high dry weight fraction of biomass through a reactor while maintaining the ability of treatment chemicals to penetrate and optimally prepare the biomass for saccharification, in addition to using minimal chemical and energy inputs, is a challenge for biomass treatment processes. Also a method that includes low capital cost equipment is desired. Methods including reactors with no requirement for stirring or reactor rotation may provide lower capital cost for equipment and lower energy input.

Systems not requiring stirring or reactor rotation and specifying means for moving biomass through a reactor have been described. U.S. Pat. No. 4,186,658 discloses an apparatus for conveying particulate material, such as wood chips, straw, bagasse and other fibrous material, which compacts the material into a solid "plug" state. A screw conveyor pre-compacts the material, with further compaction by a reciprocating piston. The compact plug is so dense that it is capable of effectively preventing blow-back within the system. The plug may then be fed to a means for processing the material. A dense plug of biomass material would not be optimally accessible by pretreatment reactants.

Similarly, U.S. Pat. No. 4,136,207 discloses a process for preparing cellulosic material with enhanced digestibility by ruminants that begins with mechanically compacting the material. It is then subjected to high steam pressure in the absence of chemical reagents, and is further compacted to form a solid plug of biomass which prevents escape of steam through the inlet. Small portions of the material are then discharged, subjecting it to rapid reduction in pressure. The compacting of biomass into a plug would not allow optimal accessibility by chemical reagents used in pretreatment.

U.S. Pat. No. 6,176,176 discloses an apparatus for treating cellulosic materials that uses a rotatable screw mounted in a barrel of an extruder. Liquid ammonia under pressure is fed into the barrel and mixed with lignocellulosic material in the barrel, then the lignocellulosic material containing the ammonia is expanded explosively by change of liquid ammonia to a gas as it exits the barrel through a heated die. Use of an extruder in a large scale commercial process would be very costly and therefore not provide an economical process.

A method for treating biomass to produce fermentable sugars which uses low strength aqueous ammonia to pretreat high concentration biomass is disclosed in co-owned and co-pending U.S. Ser. No. 11/402,757.

There remains a need for a system and/or method for treating biomass that moves high dry weight of biomass through a low-cost reactor while allowing for maximal accessibility by chemical reactants, to prepare the biomass for saccharification.

SUMMARY OF THE INVENTION

The present invention provides methods for treating biomass prior to saccharification, pretreated biomass produced by the present method, as well as hydrolysate containing fermentable sugars produced by subsequent saccharification of the pretreated biomass. In one aspect, a method for treating biomass comprises:
a) providing biomass;
b) loading the biomass of (a) using a non-compacting feeder into an apparatus comprising;
   i) a cylindrical barrel having a first end fitted with a piston and a second end fitted with a discharge valve;
   ii) optionally, an offset attached at one offset end to the cylindrical barrel near the cylindrical barrel first end, and having a sealable valve at the unattached offset end;
   iii) at least 2 sealable ports in the cylindrical barrel or in the offset;
   iv) optionally, a valve in the cylindrical barrel dividing the barrel into separate first and second chambers, said first chamber having the barrel first end fitted with said piston, and said second chamber having the barrel second end with the discharge valve; and
   v) a flash tank attached to the discharge valve at the second end of the barrel;

wherein said biomass is loaded into the cylindrical barrel or optionally into said offset attached to said cylindrical barrel;
c) closing off said cylindrical barrel and offset, if present;
d) optionally applying vacuum via at least one port in the cylindrical barrel;

e) adding through said at least one port in the cylindrical barrel or offset an aqueous solution comprising ammonia in an amount that is less than about 12 weight percent relative to dry weight of biomass in the barrel, creating a biomass and aqueous ammonia mixture, and further wherein the dry weight of biomass is at a high solids concentration of at least about 15 weight percent relative to the weight of the biomass and aqueous ammonia mixture, and adding steam through said second port in the t cylindrical barrel or offset, if present, to reach a temperature inside the barrel that is between about 85° C. and about 180° C.;

f) closing the ports in the cylindrical barrel and offset, if present, to provide an impermeable chamber;

g) holding the biomass and aqueous ammonia mixture in the impermeable chamber at suitable temperature for a time that is between about 30 seconds and about 4 hours;

h) optionally moving the biomass and aqueous ammonia mixture to a second chamber in the cylindrical barrel, if present, by displacement with said piston wherein the biomass is not compacted, and holding it for a time that is between about 2 minutes and 4 hours; and i) moving the biomass and aqueous ammonia mixture with said piston through the impermeable cylindrical barrel of (g) or (h) through the discharge valve into the flash tank;

wherein treated biomass is produced.

In another aspect, a method for treating biomass comprises:

a) providing a mixture of biomass and an aqueous solution comprising ammonia wherein the dry weight of biomass is at least about 15 weight percent relative to total weight of the biomass and aqueous ammonia mixture, and the aqueous ammonia is in an amount that is less than about 12 weight percent relative to dry weight of biomass;

b) loading the biomass and aqueous ammonia mixture of (a) using a non-compacting feeder into an apparatus comprising;
  i) a cylindrical barrel having a first end fitted with a piston and a second end fitted with a discharge valve;
  ii) optionally, an offset attached at one offset end to the cylindrical barrel near the cylindrical barrel first end, and having a sealable valve at the unattached offset end;
  iii) at least 2 sealable ports in the cylindrical barrel or in the offset;
  iv) a valve in the cylindrical barrel dividing the barrel into separate first and second chambers, said first chamber having the barrel first end fitted with said piston, and said second chamber having the barrel second end with the discharge valve; and
  v) a flash tank attached to the discharge valve at the second end of the barrel;

wherein said biomass is loaded into the first chamber of the cylindrical barrel or optionally into said offset attached to said cylindrical barrel;

c) closing off said first chamber in the barrel and the offset, if present;

d) optionally applying vacuum via said least one port;

e) adding through the least one first port in the first chamber or offset, if present, steam to reach a temperature inside the chamber that is between about 85° C. and about 180° C.;

f) closing the ports in the first chamber and offset, if present, to provide an impermeable first chamber;

g) holding the biomass and aqueous ammonia mixture in the impermeable first chamber at suitable temperature for a time that is between about 30 seconds and about 4 hours;

h) optionally, moving the biomass and aqueous ammonia mixture through an opened valve into the second chamber of the cylindrical barrel by displacement with a piston through the impermeable first chamber wherein the biomass is not compacted, i) optionally, closing the opened valve to form a second impermeable chamber and holding the biomass and aqueous ammonia mixture for a time that is between about 2 minutes and about 4 hours; and j) moving the biomass and aqueous ammonia mixture by displacement with a piston following step (g) or step (i) through the discharge valve into the flash tank;

wherein the biomass is not compacted and whereby treated biomass is produced.

Yet additional aspects of the present invention are directed to the treated biomass that has been prepared according to the present methods, and the hydrolysate containing fermentable sugars produced by saccharification of biomass that has been treated by the present method.

Biomass refers to any cellulosic and/or lignocellulosic material which may include bioenergy crops, agricultural residues, municipal solid waste, industrial solid waste, yard waste, wood, forestry waste or combinations thereof. Energy may be applied to the biomass before (a), in order to reduce the size, increase the exposed surface area, and/or increase the accessibility of cellulose, hemicellulose and/or oligosaccharides present in the biomass.

BRIEF DESCRIPTION OF THE DRAWINGS

FIG. 6 is a schematic drawing of an embodiment of a swingcheck valve gradual expansion venturi, with the valve closed in A and open in B.

DETAILED DESCRIPTION

Figure 1:
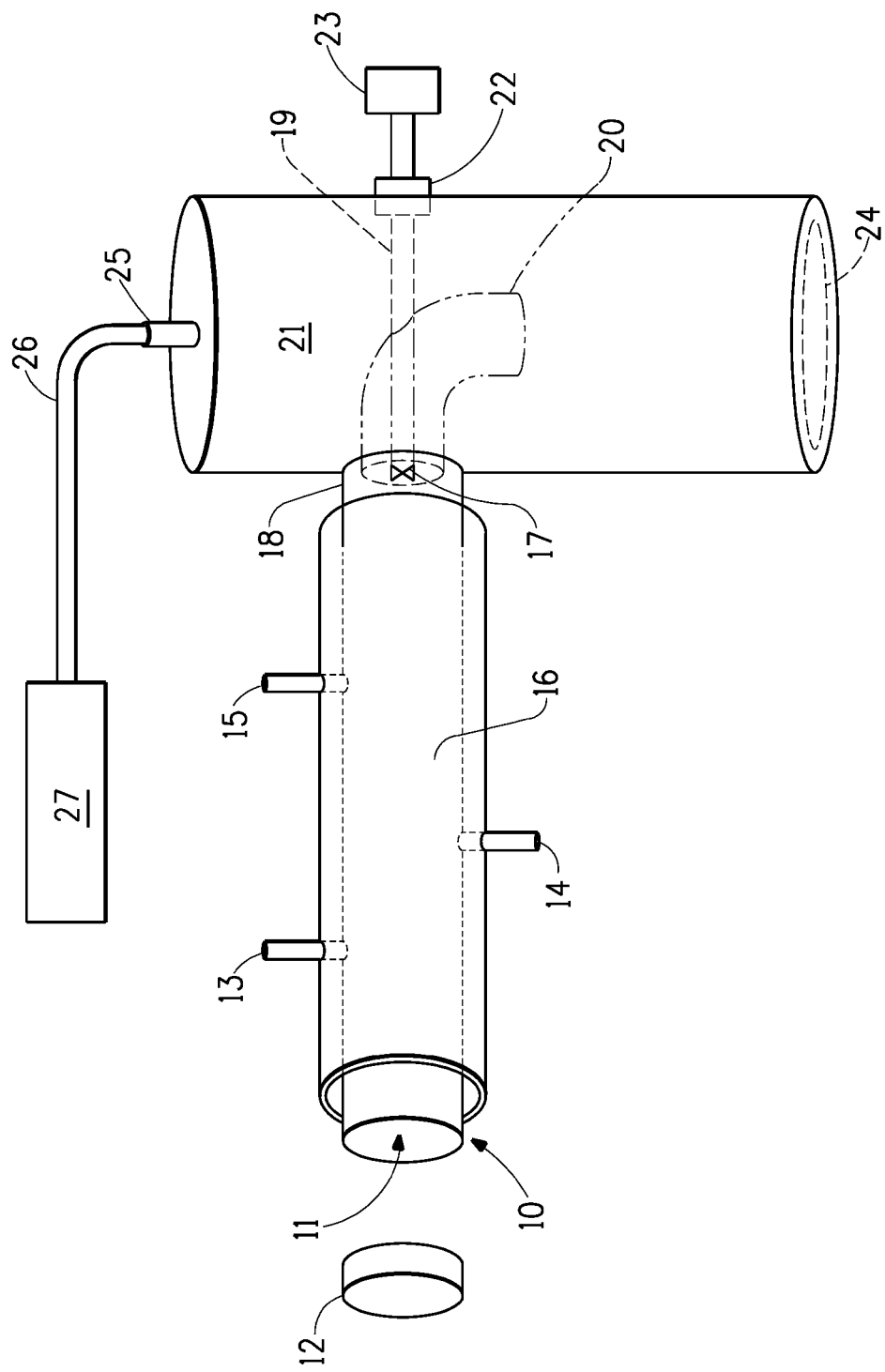
FIG. 1 is a schematic drawing of one embodiment of an apparatus for use in the present invention.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides methods for the treatment of biomass to prepare it for undergoing saccharification to produce fermentable sugars. The sugars may be fermented to produce valuable products such as fuels and other chemicals. Through the pretreatment, saccharification and fermentation steps, renewable biomass, including waste biomass, may be used to produce valuable chemicals which may decrease the need for oil.

Definitions:

In this disclosure, a number of terms are used. The following definitions are provided:

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. According to the invention, biomass may be derived from a single source, or biomass can comprise a mixture derived from more than one source; for example, biomass could comprise a mixture of corn cobs and corn stover or fiber, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, hay, rice straw, switchgrass, waste paper, sugar cane bagasse, sorghum stalks, soy hulls or stalks, components obtained from milling of grains, trees, branches, roots, leaves, wood chips, sawdust, shrubs and bushes, vegetables, fruits, flowers and ruminant animal manure. In one embodiment, biomass that is useful for the invention includes biomass that has a relatively high carbohydrate value, is relatively dense, and/or is relatively easy to collect, transport, store and/or handle. In one embodiment of the invention, biomass that is useful includes corn cobs, corn stover, corn fiber and sugar cane bagasse.

The term "fermentable sugar" or "sugars" refers to oligosaccharides and monosaccharides that can be readily fermented to target chemicals.

The term "lignocellulosic" refers to material comprising both lignin and cellulose. Lignocellulosic material may also comprise hemicellulose.

The term "cellulosic" refers to material comprising cellulose.

The term "saccharification" refers to the production of fermentable sugars from polysaccharides.

By "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

An "aqueous solution comprising ammonia" refers to the use of ammonia gas ($NH_3$), compounds comprising ammonium ions ($NH_4^+$) such as ammonium hydroxide or ammonium sulfate, compounds that release ammonia upon degradation such as urea, and combinations thereof in an aqueous medium.

The term "treatment" refers to a process of a reactant acting on a material wherein the physical and/or chemical properties of the material are altered.

The term "reactant" refers to a composition that is able to alter the physical and/or chemical properties of a target material under conditions used in a treatment process.

An "enzyme consortium" for saccharification is a combination of enzymes that are able to act on a biomass mixture to produce fermentable sugars. Typically, a saccharification enzyme consortium may comprise one or more glycosidases; the glycosidases may be selected from the group consisting of cellulose-hydrolyzing glycosidases, hemicellulose-hydrolyzing glycosidases and starch-hydrolyzing glycosidases. Other enzymes in the saccharification enzyme consortium may include peptidases, lipases, ligninases and feruloyl esterases.

The terms "treat" and "pretreat" with respect to biomass are related in the following manner. Biomass is treated with reactant to form a treated biomass product, which may also be referred to as treating to form pretreated biomass or pretreating to form pretreated biomass. The use of "pre" distinguishes the treating of biomass that is prior to saccharification of biomass.

Biomass Treatment Methods

A method for treating biomass to produce fermentable sugars which includes the use of low strength aqueous ammonia to pretreat high concentration biomass is disclosed in co-owned and co-pending U.S. application Ser. No. 11/402, 757, which is herein incorporated by reference. Applicants have developed a new method for efficiently treating biomass using low strength aqueous ammonia and high biomass concentration conditions. Applicants found the present method to be surprisingly successful due to the aspect of avoidance of compacting the biomass at any stage, and thereby allowing for improved access of treatment reactants to the biomass over that which occurs in a system that includes biomass compaction. In systems where biomass is compacted, the biomass can be de-compacted for improved reaction with treatment reactants, but this requires high energy input and thereby raises the cost of the system. In the method of the present invention, no de-compaction step or process is needed.

To reduce cost for large-scale biomass treatment, the present method has been developed in which biomass is added to a stationary apparatus without compacting, and is moved through the apparatus without compacting. By maintaining the biomass in a non-compacted state, the natural pores and channels of the biomass material are not crushed. The treatment reactants used in the present method include aqueous ammonia and steam. These reactants are able to penetrate through the non-compacted natural biomass pores and channels providing rapid and thorough effects on the cellulosic or lignocellulosic material of the biomass. This treatment method is highly effective in producing treated biomass that undergoes effective saccharification to produce fermentable sugars, in that it leads to a high conversion of biomass carbohydrates to de-polymerized sugars per enzyme dosage and reaction time.

Figure 2:
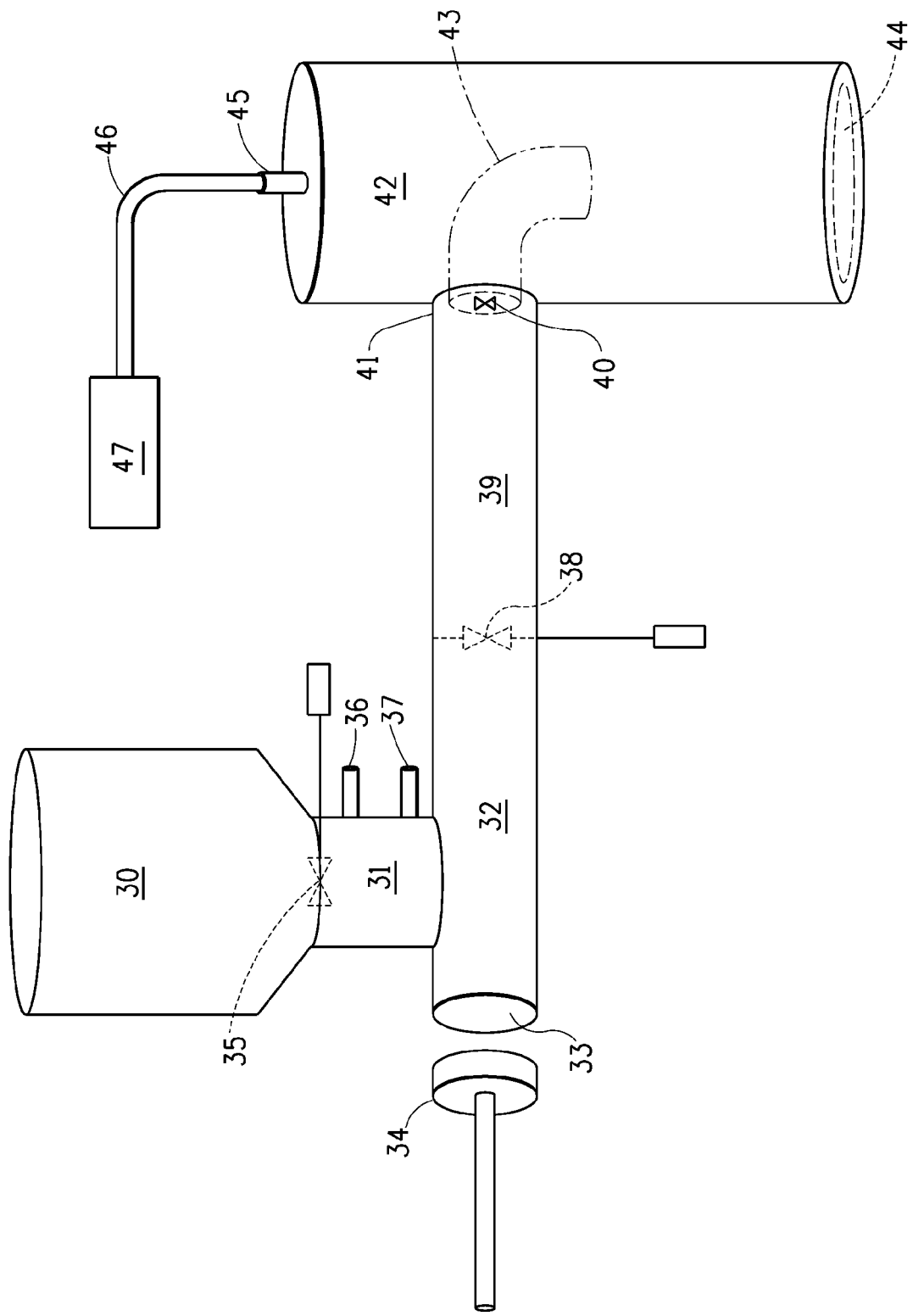
FIG. 2 is a schematic drawing of a second embodiment of an apparatus for use in the present invention.
Figure 3:
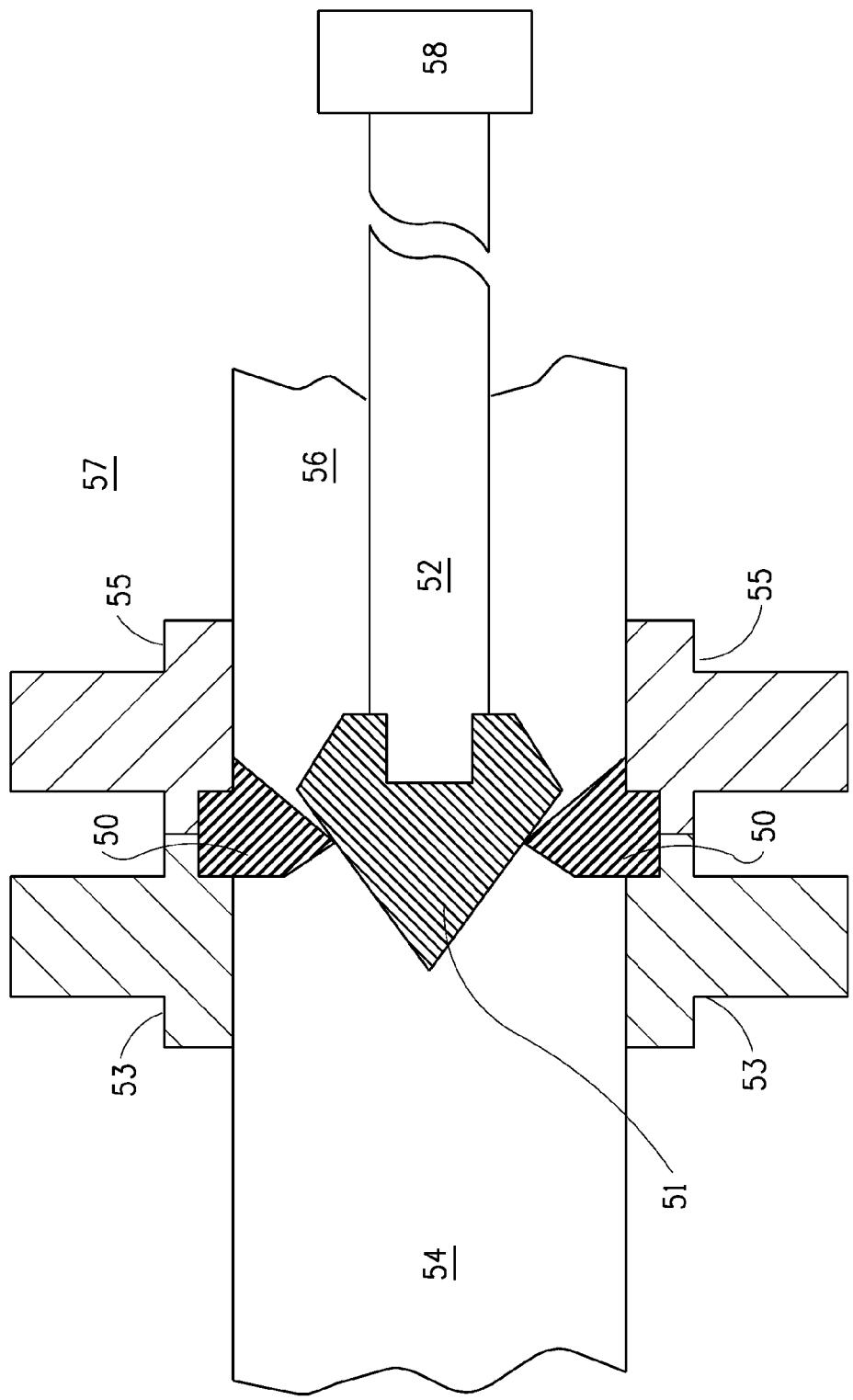
FIG. 3 is a schematic drawing of one embodiment of a gradual expansion venturi used as a discharge valve, with the valve closed.
Figure 4:
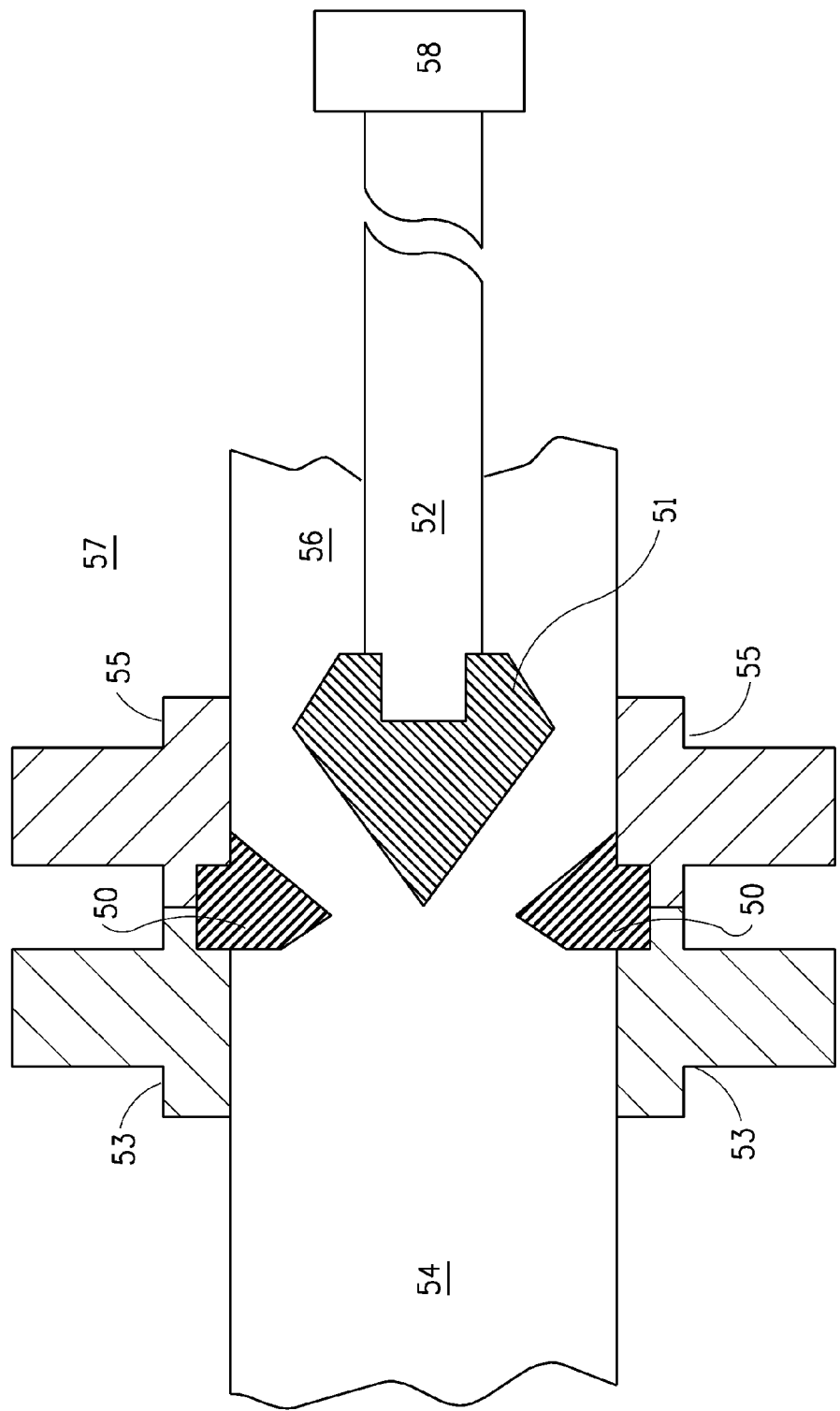
FIG. 4 is a schematic drawing of the gradual expansion venturi embodiment of FIG. 3, with the valve open.

The present biomass treatment methods may best be understood by making reference to the schematic drawings in FIGS. 1 and 2, which show two embodiments of a piston/barrel-type apparatus, and the following description of use of the apparatus in the present treatment methods. These drawings are simplified for clarity of illustration, where some elements are omitted such as the flanges shown in FIGS. 3 and 4. The apparatus in FIG. 1 is a test scale reactor. It comprises a horizontal cylindrical chamber (10) with an open first end for adding biomass (11) that is then sealed following biomass loading by inserting a moveable plug (12), which is used as a type of piston. The cylindrical chamber has a first sealable port (13) for adding aqueous solution comprising ammonia, a second sealable port (14) for adding steam to the biomass in the cylindrical chamber, and a third port (15) for applying a vacuum. Steam is injected to raise the temperature of the biomass and aqueous ammonia mixture for a treatment reaction. An insulation jacket (16) covers the cylindrical chamber.

Following loading biomass, application of vacuum, and addition of aqueous solution comprising ammonia and steam, the ports (13, 14, and 15) are sealed and a desired temperature is maintained. Following a period of time, a previously closed discharge valve (17) is opened in the cylinder second end (18) by moving the valve shaft (19). The valve shaft extends through a hole in a downward directed internal separating elbow (20) in the adjacent flash tank (21) and through a packing gland (22) on the far side of the flash tank to an actuator (23). The biomass and aqueous ammonia mixture is pushed through the discharge valve (17) by moving the plug in the cylindrical barrel first end towards the second end. The biomass passes through the discharge valve and into the flash tank (21) through the elbow (20). A cover (24) over an opening in the bottom of the flash tank allows access to pretreated biomass. A port (25) in the top of the flash tank allows exit of vapors, and is connected through a tubing (26) to a condenser (27).

Further description of an embodiment of the apparatus of FIG. 1 and its use in the present treatment methods in Examples herein is as follows. The barrel piston reactor consisted of a 5.1 cm×68.6 cm stainless steel barrel equipped with a piston, oriented horizontally. The piston was sealed to the barrel with four O-rings and was pressurized with nitrogen (up to about 5600 kPa) on the backside of the piston during the discharge stroke. The 68.6 cm barrel was equipped with eight multiple use ports, 4 each along the top and bottom surfaces, allowing application of vacuum, injection of aqueous ammonia, injection of steam, and insertion of thermocouples for measurement of temperature inside the barrel. The reactor barrel was equipped with a steam jacket for even heating of the barrel. The reactor barrel was directly attached to a 15.2 cm×61 cm stainless steel flash tank, oriented vertically. The barrel was isolated from the flash tank by a conical nozzle and seat end shearing valve arrangement. The diameter of the end valve shearing die was 3.5 cm. The backpressure on the conical nozzle and seat was adjustable, with most tests performed using ~138 kPa (gauge pressure) of backpressure into a 10.2 cm diameter air cylinder connected to the cone of the end shear valve. The cone of the end shearing valve could move back up to 1.6 cm to allow discharge of particles in the flash tank. An elbow at the outlet of the end shear valve directed the treated solids down into the bottom of the flash tank where the solids were easily removed by unbolting a domed end flange in the bottom of the tank. An upper domed flange to the flash tank incorporated a special outlet fitting with slots machined at right angles to the axis of the flash tank, which caused released vapors to travel around a corner path to an exit fitting, helping to prevent carry-over of entrained biomass particles and water droplets into a vent condenser. Three electrical band heaters (set at 60° C.) and insulation were added along the flash tank to allow hot treated solids to flash into a heated vessel, better simulating a commercial scale process.

In another embodiment a small barrel piston reactor was built as described above, except having a 45.7 cm barrel, no steam jacket, three electrical band heaters, a 2.5 cm thick fiberglass mat covered with a silicone impregnated fiberglass jacket as insulation, and three multiple use ports. Other features including the flash tank, shearing valve, and elbow were as described for the large barrel piston reactor.

The apparatus in FIG. 2 is a commercial scale reactor design. It comprises a horizontal cylindrical barrel fitted with a piston (34) at the first end (33) and a discharge valve (40) at the second end (41). The barrel is insulated and has impermeable walls. An offset (31) is attached near the first end and a valve (35), that is an infeed valve, is located at the unattached end of the offset. A hopper (30) is attached to the valve end of the offset. Biomass is added through the hopper. There may be non-compacting flow-inducing means to control biomass addition from the hopper (30) to the offset (31). The offset has a first sealable port (36) and a second sealable port (37) for adding aqueous ammonia and steam to the biomass in the offset as it moves into the cylindrical barrel. A second valve (38) separates the barrel into a first cylindrical chamber (32) and a second cylindrical chamber (39). Biomass and aqueous ammonia mixture pass through the offset into the first chamber where a desired temperature and pressure is reached by addition of steam. Movement of the piston through the impermeable barrel pushes the biomass and aqueous ammonia mixture from the first chamber into the second chamber, through the opened second valve (38), and displacing contents in the second chamber (39) through the opened discharge valve (40) into a flash tank (42). Contents of the second chamber are biomass and aqueous ammonia mixture that were previously moved into this chamber and held for as long as necessary for the treatment reaction under the conditions used. The second valve (38) is then closed and the piston (34) is retracted so as to prepare the first cylindrical chamber (32) to be reloaded and the process cycle repeated. In the flash tank (42), the biomass moves through a downward directed elbow (43). A cover (44) over an opening in the bottom of the flash tank allows access to pretreated biomass. A port (45) in the top of the flash tank allows exit of ammonia vapors, and is connected through a tubing (46) to a condenser (47).

The apparatus may be constructed using carbon steel or stainless steel. The cylindrical barrel may be horizontal as depicted in FIGS. 1 and 2, or it may be vertical. With a vertical barrel the offset and hopper as shown in FIG. 2 would be reconfigured to allow loading of biomass into the barrel chamber, such as at a less than 90 degree angle. One skilled in the art would be able to readily configure the apparatus with a vertical barrel. For example, the vertical barrel may be located above the flash tank and be connected without an elbow directing flow downward, since flow through the discharge valve would already be directed downward. It is also within the ability of one skilled in the art to orient the flash tank in a vertical or horizontal manner. A vertical tank is more suitable in the present methods with ammonia treatment to facilitate removal and capture of ammonia gas released in the flash tank.

The two embodiments of FIGS. 1 and 2 function similarly in that biomass is added to and moved through the reactors without compaction. The embodiment of FIG. 1, with one chamber, is a batch system for processing one sample of biomass at a time. The embodiment of FIG. 2, with two chambers that are separated by a valve, allows a semi-continuous or fed-batch operation wherein multiple loadings of biomass are processed concurrently. In this second embodiment, each piston displacement cycle, where each successive loading of biomass enters the second chamber, is accompanied by the discharge of corresponding volume through the discharge orifice once the second chamber is fully loaded. The number of piston displacement cycles in the second chamber at one time, and therefore the size of the second chamber, is related to the residence time required for each biomass sample. Residence time is discussed further below in relation to temperature and time for treatment in the present methods.

The present methods are particularly suited to treatment of biomass at a high dry weight of biomass relative to the weight of biomass, aqueous ammonia, and steam mixture of the treatment reaction. It is desirable to treat biomass in a high dry weight concentration to provide biomass that will produce a high sugars concentration hydrolysate following saccharification. The features of the present method that provide that the biomass is not compacted allow effective treatment of high dry weight concentration of biomass. The initial dry weight of biomass used in the present methods is at least about 15% of the total weight of the biomass and aqueous ammonia mixture. More typically, the dry weight of biomass is at least about 20%, and may be at least about 30%, 45%, 50%, or more. The percent dry weight of biomass may vary and the optimal percent may be different for different types of biomass. For example, biomass of at least about 24% is desired when using corn cob, to provide pretreated biomass that is saccharified to produce fermentable sugars concentrated sufficiently for cost-effective fermentation to ethanol. More suitable is corn cob biomass that is at least about 30%. The preferred percent dry weight of a particular type of biomass for use in the present methods for producing a high sugars hydrolysate is readily determined by one skilled in the art.

The biomass may be used directly as obtained from a source, or energy may be applied to the biomass to reduce the size, increase the exposed surface area and/or increase the availability of cellulose, hemicellulose, and/or oligosaccharides present in the biomass. Energy means useful for this purpose include those that do not crush or compact the biomass, such that the ultrastructure of the biomass is not destroyed. For example, biomass may be shredded, chopped, or chipped. A jaw crusher may also be used when used in a manner that shears the biomass without crushing the ultrastructure. A tooth disk refiner is also useful for reducing the biomass size prior to pretreatment in the present methods.

In the present treatment methods biomass is moved into a cylindrical barrel using a non-compacting feeder. In the simplest case a non-compacting feeder refers to loading biomass by hand into an open first end of the cylindrical barrel. If there are two chambers in the barrel, loading is into the first chamber. This method is described in examples herein using a reactor as set forth in FIG. 1. The non-compacting feeder exemplified in the reactor of FIG. 2 is a hopper. The hopper may be self-dumping, and/or it may be equipped with a flow-inducing device that does not provide compacting force. For example various types of live-bottom bin flow inducers followed by flow metering conveyors such as various types of drag chains, bucket elevators, or rotating helixes (such as Acrison® devices) may be used. The amount of biomass loaded in the first cylindrical chamber is limited so that room is allowed for biomass expansion, which may occur upon addition of aqueous ammonia and steam.

Vacuum may be applied to the cylindrical barrel containing biomass. If there are two chambers in the barrel, vacuum is applied to the first chamber containing biomass. Typically if applied, the vacuum reduces the pressure to less than about 20 kPa. An aqueous solution comprising ammonia is added through one or more ports in the cylindrical barrel, or its offset, in an amount so that ammonia is less than about 12 weight percent relative to dry weight of biomass in the chamber. It is more suitable to use more than one port, with ports being distributed so that ammonia solution contact is substantially evenly distributed to the biomass. If there are two chambers in the barrel, ammonia solution is added to the first chamber containing biomass. Also it is more suitable that the ammonia is in an amount that is between about 4% and about 6% relative to dry weight of biomass in the chamber. The ammonia solution may be preheated, which will contribute to raising the temperature of the biomass. In an alternative embodiment, the aqueous ammonia solution is mixed with the biomass prior to loading into the first cylindrical chamber. Biomass and aqueous ammonia may be mixed in a vessel that feeds into the first cylindrical chamber. For example, aqueous ammonia may be pumped through an inline heater and into a paddle mixer containing biomass. The biomass and aqueous ammonia mixture is then fed into the first cylindrical chamber, where steam is injected after closing off the chamber. Alternatively, biomass, ammonia, and steam may be premixed and added to the first cylindrical chamber. At the temperatures and pressures described below, much of the aqueous ammonia will evaporate to vapor which permeates the biomass being pretreated. In addition, recycled wet ammonia vapor that is collected from the flash tank may be injected to form a part of the total added ammonia.

In the present method, the aqueous solution comprising ammonia may optionally comprise at least one additional base, such as sodium hydroxide, sodium carbonate, potassium hydroxide, and potassium carbonate. The at least one additional base may be added at up to 10 weight percent relative to dry weight of biomass. Additional base(s) may be utilized, for example, to neutralize acids in biomass, to provide metal ions for the saccharification enzymes or to provide metal ions for fermentation growth medium.

Since biomass is not compacted in the present method, it cannot block the passage of steam as occurs in systems with compacted biomass. Therefore the chamber to which steam is added is closed off prior to steam injection. Ports, other than the one or more through which steam is being added, are sealed. The barrel first end piston, or plug serving as a piston, is put in place and valves are closed. Valves used may be any opening and closing type of valve, such as poppet-valves or rotating knife-gate valves.

Steam is added through one or more ports in the cylindrical barrel, or the offset, in an amount that is needed to raise the temperature of the biomass and aqueous ammonia mixture to the desired point. If there are two chambers in the barrel, steam is added to the first chamber containing biomass. It is more suitable to use more than one port, with ports being spaced so that steam contact is distributed over the biomass. Steam is added to raise the temperature of the biomass and aqueous ammonia mixture to between about 85° C. and about 180° C. Additional steam may be added through a port in the second cylindrical chamber when present, if needed to maintain the desired temperature. The apparatus may include a heating jacket, steam jacket, band heaters or insulation jacket to contribute to raising and/or maintaining the temperature. Heating or steam jackets are particularly suited to small scale reactors while insulation jackets are suited to large scale reactors. Heating may occur at different stages, including preheating the barrel prior to treating or pretreating.

At temperatures below 85° C., the time required for treatment with low strength aqueous ammonia would be prohibitively long. The time needed for treatment decreases as the temperature increases. For example, treatment at 85° C. may be for between about two and about four hours, while treatment at 180° C. may be only a few minutes. Function of the batch feeding cycle as used in the reactor of FIG. 2 requires adequate time for multiple loadings. It is therefore desirable to choose a time and temperature combination that has limited time, which is long enough for function of the reactor embodiment used, yet a moderate temperature to provide an economical process. With moderate temperatures, lower pressure steam, which has lower cost, may be used. More suitable conditions are treatment at between about 120° C. and about 160° C. for between about 60 minutes and about 5 minutes, with time decreasing as temperature increases. Particularly suitable conditions are treatment at between about 140° C. and about 150° C. for between about 30 minutes and about 10 minutes, with time decreasing as temperature increases. The type of biomass being pretreated also can affect the optimum time and temperature for treatment in the present method, as can readily be assessed by one skilled in the art.

The time that biomass is held at the desired temperature within a reactor chamber is the residence time. When using a reactor with only a first chamber, the residence time takes place in the first chamber. When using a reactor with a first chamber and a second chamber, time in the first chamber may be only long enough to combine biomass with reactants prior to moving the mixture to the second chamber, with residence time occurring in the second chamber. In this case time in the first chamber may be as little as about 30 seconds, and time in the second chamber may be between about 2 minutes and 4 hours.

Bringing the biomass to the described temperatures using steam in the present methods results in pressures within the reactor chamber that are between about 60 kPA and about 750 kPa. More typically, pressure is between about 300 kPA and 600 kPA. These are relatively low pressures with respect to other known pretreatment methods such as the AFEX method described in U.S. Pat. No. 5,037,663, where pressures of 1150 kPa to 4250 kPa are used, or methods using a steam gun as described in U.S. Pat. No. 4,461,648 where pressures of about 1800 kPa to about 5600 kPa are presented in FIG. 1 therein. Operation of the present methods at the more moderate pressures provides a lower cost system, since lower pressure steam may be used.

In the present methods biomass is moved through the first chamber and, if present, the second chamber, without compaction. This may be achieved using a piston and impermeable cylinder chamber. For purposes of the present disclosure, a piston may include any article that may be used as a piston such as a plug that is pushed into the chamber, as well as any type of standard piston. The plug of a type of reactor as exemplified in FIG. 1 may be pushed into the chamber using any method that applies adequate pressure to move the biomass. A particularly suitable method is to provide a static closure at the end of the chamber after inserting the plug, such as a bolted cylinder head, then to introduce nitrogen between the closure and the plug to build up pressure and move the plug. The plug may be moved by other means, such as using a pushrod connected to a hydraulic, pneumatic, or electric actuator.

The barrel of the apparatus is impermeable (with all ports and valves closed) in that there are no unsealed wall penetrations, so liquid does not leave the barrel. Retention of liquid allows the piston to move the biomass without compacting it. Liquid in the present treatment methods is limited, and what is there may serve to lubricate the chamber walls to enable non-compacting flow in response to piston pressure. In fact, piston pressure may temporarily slightly squeeze the biomass, as with a sponge, without being squeezed enough that the biomass pores and channels are collapsed. Upon removing the piston pressure, the biomass may reabsorb the liquid into the pores and channels that have not been crushed. To aid in biomass flow, a lubricating liquid such as vegetable oil soap may be introduced into the chamber. Flow may be enhanced by rifling of the internal chamber wall, wherein adding discontinuities such as angled grooves may reduce friction, thereby reducing yield stress and improving biomass flow. Movement of biomass without compaction maintains the swollen liquid-filled pores generated by treatment, which enhances subsequent saccharification.

In the present methods, following treatment for the desired time at the desired temperature, the biomass and aqueous ammonia mixture is moved through a discharge valve at the end of the cylindrical barrel into a flash tank. The discharge valve is closed during biomass reaction with aqueous ammonia at the desired temperature, then opened for passage of the biomass. In a double chamber reactor, as exemplified in FIG. 2, the discharge valve opens in synchronism with the opening of the valve between the first and second chambers, after the piston has built up pressure in the first chamber in order to displace the entire contents of the second chamber by the volume of the first chamber's contents.

Discharge valves which may be used are exemplified by rotary V-port valves, swingcheck valves, and poppet discharge valves. Particularly useful in a smaller scale reactor, as exemplified in FIG. 1, is a piston-operated poppet-type discharge valve, where the hardfaced upstream side of the valve seat is the discharge orifice, and the softer downstream side of the valve seat seals against a hardfaced valve plunger, with the flow area increasing continually beyond the valve seat when the valve plunger is retracted to open.

Most suitably the poppet-type discharge valve would incorporate a gradual expansion venturi. One embodiment of a gradual expansion venturi poppet valve, that is suitable for a small scale reactor as exemplified in FIG. 1, is diagrammed in FIG. 3. This valve incorporates a conical nozzle and a seat end shearing valve arrangement. To avoid plugging, the gradual expansion venturi as exemplified in FIG. 3 (closed position) and FIG. 4 (open position) was designed to accelerate solids through a steadily enlarging gap between the stationary outside cone of the venturi (50) and the moveable inside cone of the venturi (51) that is mounted on the end of a valve shaft (52). The venturi outside cone is a generally-toroidal venturi-shape clamped between a flange (53) at the reactor chamber (54; equivalent to 10 in FIG. 1) exit and a flash tank inlet flange (55). The venturi inside cone (51) is the nose on the end of the reactor exit valve shaft (52). The venturi inside cone and valve shaft are within the discharge elbow (56; equivalent to 20 in FIG. 1) that is within the flash tank (57; equivalent to 21 in FIG. 1). The valve shaft is attached to an actuator (58) for control of movement. The actuator may be any device that is able to move the valve shaft back and forth in a horizontal motion, such as an electric, pneumatic or hydraulic motor, pneumatic valve actuator, or hydraulic piston. When the valve shaft is in its farthest leftward position the outer edge of the inside cone seats against the inner edge of the outside cone to seal the discharge end of the reactor during treatment. When it is time to discharge the reactor, the valve shaft is moved to the right to provide the size of opening that is desired for the flash venturi.

This design provides a flash zone of some length which expands smoothly in the direction of flow. In this design, biomass solids are accelerated down the axis of the gradually-opening annular cone, which avoids allowing sudden radial expansion leading to plugging.

Figure 5:
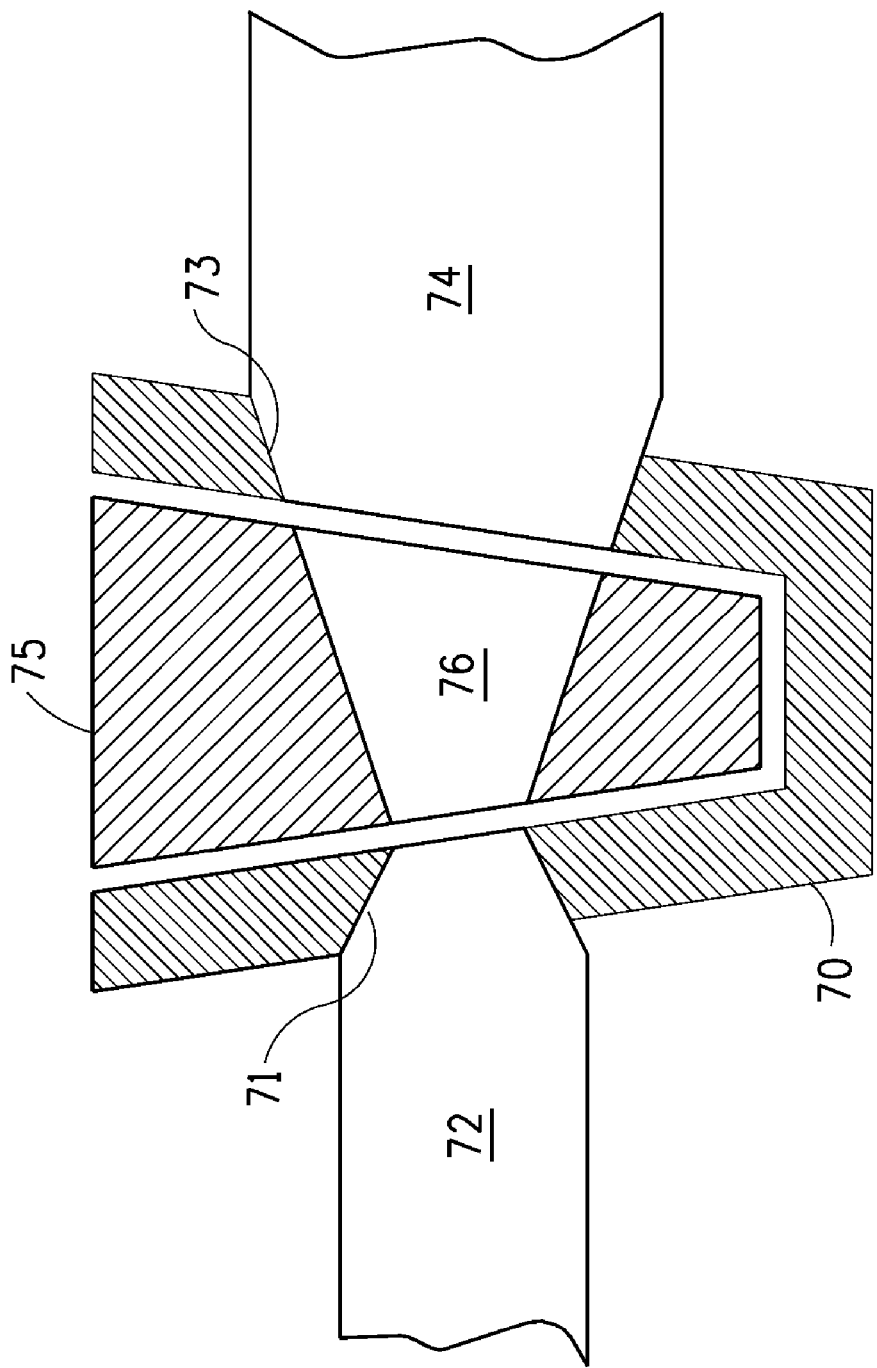
FIG. 5 is a schematic drawing of an embodiment of a V-port valve gradual expansion venturi.

Another embodiment of a gradual expansion venturi, that is suitable as a discharge valve particularly in a larger scale reactor as exemplified in FIG. 2, is diagrammed in FIG. 5. This is an embodiment of a V-port plugcock where the flash venturi expansion is machined into the valve body. Within the flash venturi stationary body (70) there is a narrowing (71) from the exit end of the reaction chamber (72) and an expansion (73) to the entrance to the flash tank (74). In the rotary core (75) of the plugcock is an angled opening (76) that aligns with the reactor chamber narrowing (71) and the expansion to the flash tank (73) when in the open position. The rotary core (75) is turned in a half of a full rotation to block alignment of the plugcock which closes the valve.

A further embodiment of a gradual expansion venturi, that is suitable as a discharge valve, particularly in a larger scale reactor as exemplified in FIG. 2, is diagrammed in FIG. 6. This is an embodiment of a swingcheck valve that has a cone (80) which fits into the narrowed junction (81) between the reactor chamber (72) and the entrance to the flash tank (74) (FIG. 6A). The cone is on an arm (82) that is attached to a shaft (83) that extends through a packing gland to a rotary valve actuator. The shaft is rotated in the direction of the dotted arrow to move the arm counterclockwise to open the junction, forming a gradual expansion venturi (FIG. 6B). In another embodiment of a swingcheck valve used for a gradual expansion venturi, the cone may be several feet in diameter, with the distance moved counterclockwise to open the valve being only a few inches, which is less than 8 cm.

Biomass and ammonia mixture moving through the discharge valve enters a flash tank, which is able to hold a vacuum. In the flash tank ammonia is released from the treated biomass and the biomass is cooled, in preparation for saccharification. Any typical flash tank may be used, with one having a tangential or volute entrance that provides the function of a separating elbow most suitable. It is particularly suitable to impose flashing several times in sequence at different pressures to release ammonia from the pretreated biomass. For example, a first flash to a pressure near atmospheric typically removes most of the free ammonia and cools material to about 100° C. A second flash to a pressure less than about 20 kPa removes the remaining free ammonia and cools material to a temperature of about 50° C., which is desired for saccharification.

Ammonia vapor, released in the flash tank from the biomass and ammonia mixture passed through the discharge valve, may be recovered from the flash tank, and may be recycled. Vapor from lower-pressure flashes may be recycled using a standard vapor recompression apparatus (such as a turbine or a steam jet pump) without intercooling. Thus ammonia vapor may be recycled directly to treatment without condensation, or it may be condensed prior to re-use. In the latter case, collected vapor is fed to a condenser as in FIG. 1.

Reducing the ammonia in the treated biomass will lower the pH and reduce the amount of acid needed to reach a pH that is satisfactory for activity of saccharification enzymes. This is desirable since the extensive addition of acid may result in the formation of salts at concentrations that are inhibitory to saccharification enzymes or to microbial growth. On the other hand, ammonia left in the biomass may serve as a nitrogen source to support growth of microorganisms during fermentation. Thus remaining ammonia may reduce or eliminate the need to supplement the growth medium used during fermentation with a nitrogen source. Typically, at least a portion of the ammonia is removed, which reduces the pH but leaves some nitrogen that provides this nutrient for use in subsequent fermentation.

As the pretreated biomass accumulates at the bottom of the flash tank, it may be stirred by a paddle mixer that may be attached at the bottom of the flash tank. Pretreated biomass is removed from the bottom of the flash tank, typically by opening a cover in the bottom of the tank. A live-bottom mechanical means for extracting the pretreated biomass continuously is particularly suitable. For processing of multiple batches of biomass in the present apparatus, one batch of biomass and ammonia may be in the barrel chamber, while another batch is in the flash tank. In the two chamber apparatus, batches may concurrently be in both chambers and in the flash tank. In addition, multiple batches of pretreated biomass may be collected in the flash tank prior to removal.

Following treatment, the product typically comprises a mixture of ammonia, partially degraded biomass and some fermentable sugars. The entire pretreated biomass comprising both soluble and insoluble fractions may be removed from the flash tank and utilized in a saccharification reaction. Alternatively, some liquid may be drained from the pretreated biomass mixture prior to saccharification so that the dry weight of biomass remains high in the saccharification reaction. Excess liquid may be present following treatment, particularly when large amounts of steam are required to raise and maintain the temperature of the biomass for treatment.

In another alternative, biomass solids may be recycled through treatment in the present method.

Saccharification

Biomass treated in the present methods is further hydrolyzed in the presence of saccharification enzymes, which may be referred to as a saccharification enzyme consortium, to release oligosaccharides and/or monosaccharides in a hydrolysate. Saccharification enzymes and methods for biomass treatment are reviewed in Lynd, L. R., et al. (Microbiol. Mol. Biol. Rev. (2002) 66:506-577).

Prior to saccharification, the pretreated biomass may be treated to alter the pH, composition or temperature such that the enzymes of the saccharification enzyme consortium will be active. The pH may be altered through the addition of acids in solid or liquid form. Alternatively, carbon dioxide ($CO_2$), which may be recovered from fermentation, may be utilized to lower the pH. For example, $CO_2$ may be collected from a fermenter and fed into the pretreatment product headspace in the flash tank or bubbled through the pretreated biomass if adequate liquid is present while monitoring the pH, until the desired pH is achieved. The temperature may be brought to a temperature that is compatible with saccharification enzyme activity, as noted below. Any cofactors required for activity of enzymes used in saccharification may be added.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities.

Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. The pH optimum can range from about 2 to about 11. In another embodiment, the pH optimum used with the saccharification enzyme consortium in the present method ranges from about 4 to about 10.

The saccharification can be performed for a time of about several minutes to about 120 hr, and preferably from about several minutes to about 48 hr. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The degree of solubilization of sugars from biomass following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem. (1959) 31:426-428). Alternatively, sugars can be measured by HPLC using an appropriate column as described herein in the General Methods section.

Fermentation

Fermentable sugars released from biomass can be used by suitable microorganisms to produce target chemicals. Following saccharification, but prior to fermentation, the saccharification mixture may be concentrated by evaporation, for example, to increase the concentration of fermentable sugars. Optionally, liquid in the saccharification product may be separated from solids in a batch or continuous method. Optionally, the liquid or the entire saccharification product may be sterilized prior to fermentation. Depending on the microorganism(s) used during fermentation and the pH used during saccharification, the pH may be adjusted to that suitable for fermentation. In addition, the saccharification mixture may be supplemented with additional nutrients required for microbial growth. Supplements may include, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction. Also additional sugars may be included to increase the total sugar concentration. The saccharification mixture may be used as a component of a fermentation broth, for example, making up between about 100% and about 10% of the final medium Temperature and/or headspace gas may also be adjusted, depending on conditions useful for the fermentation microorganism(s). Fermentation may be aerobic or anaerobic. Fermentation may occur subsequent to saccharification, or may occur concurrently with saccharification by simultaneous saccharification and fermentation (SSF). SSF can keep the sugar levels produced by saccharification low, thereby reducing potential product inhibition of the saccharification enzymes, reducing sugar availability for contaminating microorganisms, and improving the conversion of pretreated biomass to monosaccharides and/or oligosaccharides.

Target chemicals that may be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, and sorbitol. Acids include acetic acid, lactic acid, propionic acid, 3-hydroxypropionic, butyric acid, gluconic acid, itaconic acid, citric acid, succinic acid and levulinic acid. Amino acids include glutamic acid, aspartic acid, methionine, lysine, glycine, arginine, threonine, phenylalanine and tyrosine. Additional target chemicals include methane, ethylene, acetone and industrial enzymes.

The fermentation of sugars to target chemicals may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and include *Escherichia, Zymomonas, Saccharomyces, Candida, Pichia, Streptomyces, Bacillus, Lactobacillus,* and *Clostridium*. In another embodiment, biocatalysts may be selected from the group consisting of recombinant *Escherichia coli, Zymomonas mobilis, Bacillus stearothermophilus, Saccharomyces cerevisiae, Clostridia thermocellum, Thermoanaerobacterium saccharolyticum,* and *Pichia stipitis*

Many biocatalysts used in fermentation to produce target chemicals have been described and others may be discovered, produced through mutation, or engineered through recombinant means. Any biocatalyst that uses fermentable sugars produced from saccharification of treated biomass using the present methods may be used to make the target chemical(s) that it is known to produce by fermentation.

Particularly of interest are biocatalysts that produce biofuels including ethanol and butanol. For example, fermentation of carbohydrates to acetone, butanol, and ethanol (ABE fermentation) by solventogenic *Clostridia* is well known (Jones and Woods (1986) Microbiol. Rev. 50:484-524). A fermentation process for producing high levels of butanol, also producing acetone and ethanol, using a mutant strain of *Clostridium acetobutylicum* is described in U.S. Pat. No. 5,192,673. The use of a mutant strain of *Clostridium beijerinckii* to produce high levels of butanol, also producing acetone and ethanol, is described in U.S. Pat. No. 6,358,717. Co-owned and co-pending patent applications WO 2007/041269 and WO 2007/050671, which are herein incorporated by reference, disclose the production of 1-butanol and isobutanol, respectively, in genetically engineered microbial hosts. Co-owned and co-pending U.S. patent application Ser. Nos. 11/741,892 and 11/741,916, which are herein incorporated by reference, disclose the production of 2-butanol in genetically engineered microbial hosts. Isobutanol, 1-butanol or 2-butanol may be produced from fermentation of hydrolysate produced using the present methods by a microbial host following the disclosed methods.

Genetically modified strains of *E. coli* have also been used as biocatalysts for ethanol production (Underwood et al., (2002) Appl. Environ. Microbiol 68:6263-6272). A genetically modified strain of *Zymomonas mobilis* that has improved production of ethanol is described in US 2003/0162271 A1. A further engineered ethanol-producing strain of *Zymomonas mobilis* and its use for ethanol production are described in co-owned and co-pending U.S. patent applications 60/847,813 and 60/847,856, respectively, which are herein incorporated by reference. Ethanol may be produced from fermentation of hydrolysate produced using the present methods by *Zymomonas mobilis* following the disclosed methods.

Lactic acid has been produced in fermentations by recombinant strains of *E. Coli* (Zhou et al., (2003) Appl. Environ. Microbiol. 69:399-407), natural strains of *Bacillus* (US20050250192), and *Rhizopus oryzae* (Tay and Yang (2002) Biotechnol. Bioeng. 80:1-12). Recombinant strains of *E. Coli* have been used as biocatalysts in fermentation to produce 1,3 propanediol (U.S. Pat. No. 6,013,494, U.S. Pat. No. 6,514,733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. Coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. Coli* (Yokota et al., (1994) Biosci. Biotech. Biochem. 58:2164-2167). Recombinant strains of *E. Coli* have been used as biocatalysts for production of para-hydroxycinnamic acid (US20030170834) and quinic acid (US20060003429).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17cr1 (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:1136-43). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-UI-Haq et al., (2005) Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid 3-hydroxyvaleric acid, were produced by recombinant *Pseudomonas putida* and *Ralstonia eutropha* (Gorenflo et al., (2001) Biomacromolecules 2:45-57). L-2,3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium, Brevibacterium*, and *Serratia*. For example, production of histidine using a strain resistant to a histidine analog is described in Japanese Patent Publication No. 56008596 and using a recombinant strain is described in EP 136359. Production of tryptophan using a strain resistant to a tryptophan analog is described in Japanese Patent Publication Nos. 47004505 and 51019037. Production of isoleucine using a strain resistant to an isoleucine analog is described in Japanese Patent Publication Nos. 47038995, 51006237, 54032070. Production of phenylalanine using a strain resistant to a phenylalanine analog is described in Japanese Patent Publication No. 56010035. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 54037235 and 57150381) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant strain of *Corynebacterium lilium* (Kumar et al, (2005) Bioresour. Technol. 96: 287-294).

Useful peptides, enzymes, and other proteins have also been made by biocatalysts (for example, in U.S. Pat. No. 6,861,237, U.S. Pat. No. 6,777,207, U.S. Pat. No. 6,228,630).

The pretreatment and saccharification of biomass to fermentable sugars, followed by fermentation of the sugars to a target chemical is exemplified in Example 5 herein for the production of ethanol from pretreated corn cobs using *Z. mobilis* as the biocatalyst for the fermentation of sugars to ethanol. The method of the present invention can also be used for the production of 1,3-propanediol from biomass. Biomass treated using the present methods may be saccharified; following saccharification, *E. coli* is used to produce 1,3-propanediol as described in Example 10 of co-owned and co-pending U.S. application Ser. No. 11/403,087, which is herein incorporated by reference.

Target chemicals produced in fermentation by biocatalysts may be recovered using various methods known in the art. Products may be separated from other fermentation components by centrifugation, filtration, microfiltration, and nano-filtration. Products may be extracted by ion exchange, solvent extraction, or electrodialysis. Flocculating agents may be used to aid in product separation. As a specific example, bioproduced 1-butanol may be isolated from the fermentation medium using methods known in the art for ABE fermentations (see for example, Durre, *Appl. Microbiol. Biotechnol.* 49:639-648 (1998), Groot et al., Process. Biochem. 27:61-75 (1992), and references therein). For example, solids may be removed from the fermentation medium by centrifugation, filtration, decantation, or the like. Then, the 1-butanol may be isolated from the fermentation medium using methods such as distillation, azeotropic distillation, liquid-liquid extraction, adsorption, gas stripping, membrane evaporation, or pervaporation. Purification of 1,3-propanediol from fermentation media may be accomplished, for example, by subjecting the reaction mixture to extraction with an organic solvent, distillation, and column chromatography (U.S. Pat. No. 5,356,812). A particularly good organic solvent for this process is cyclohexane (U.S. Pat. No. 5,008,473). Amino acids may be collected from fermentation medium by methods such as ion-exchange resin adsorption and/or crystallization.

EXAMPLES

General Methods and Materials

The following abbreviations are used:

"HPLC" is High Performance Liquid Chromatography, "C" is Centigrade, "kPa" is kiloPascal, "m" is meter, "mm" is millimeter, "kW" is kilowatt, "µm" is micrometer, "µL" is microliter, "mL" is milliliter, "L" is liter, "min" is minute, "mM" is millimolar, "cm" is centimeter, "g" is gram, "kg" is kilogram, "wt" is weight, "hr" is hour, "temp" or "T" is temperature, "theoret" is theoretical, "pretreat" is pretreatment, "DWB" is dry weight of biomass, "ASME" is the American Society of Mechanical Engineers, "s.s." is stainless steel, in" or """ is inch.

Sulfuric acid, ammonium hydroxide, acetic acid, acetamide, yeast extract, glucose, xylose, sorbitol, $MgSO_4.7H_2O$, phosphoric acid and citric acid were obtained from Sigma-Aldrich (St. Louis, Mo.).

Treatment is referred to as pretreatment in the Examples.

Small Barrel Piston Reactor

A small barrel piston reactor (piston/barrel reactor) was constructed that consisted of a 5.1 cm×45.7 cm stainless steel barrel equipped with a piston, oriented horizontally. The piston was sealed to the barrel with four O-rings and was pressurized with nitrogen on the backside of the piston during the discharge stroke. The 45.7 cm barrel was equipped with three multiple use ports allowing application of vacuum, injection of aqueous ammonia, injection of steam, and insertion of thermocouples for measurement of temperature inside the barrel. To avoid excess steam condensation upon steam injection, the outside of the barrel was heated with three band heaters and insulated with a 2.5 cm thick fiberglass mat covered with a silicone impregnated fiberglass jacket.

The reactor barrel was directly attached to a 15.2 cm×61 cm stainless steel flash tank, oriented vertically. The barrel was isolated from the flash tank by a conical nozzle and seat end shearing valve arrangement. The diameter of the end shearing valve die was 3.5 cm. The backpressure on the conical nozzle and seat was adjusted to about 138 kPa (gauge pressure) of backpressure into a 10.2 cm diameter air cylinder connected to the cone of the end shear valve. The cone of the end shearing valve could move back up to 1.6 cm to allow discharge of particles in the flash tank. An elbow at the outlet of the end shear valve directed the pretreated solids down into the bottom of the flash tank where the solids were easily removed by unbolting a domed end flange in the bottom of the tank. An upper domed flange to the flash tank incorporated a special outlet fitting with slots machined at right angles to the axis of the flash tank which caused released vapors to travel around a corner path to an exit fitting, helping to prevent carry-over of entrained biomass particles and water droplets into a vent condenser.

Large Barrel Piston Reactor

A second barrel for the piston reactor (ASME code stamped) was fabricated with the same 5.1 cm diameter, but a longer 68.6 cm length to hold additional biomass volume. The piston was sealed to the barrel with four O-rings and was pressurized with nitrogen on the backside of the piston during the discharge stroke. The 68.6 cm barrel was equipped with eight multiple use ports, 4 each along the top and bottom surfaces, allowing application of vacuum, injection of aqueous ammonia, injection of steam, and insertion of thermocouples for measurement of temperature inside the barrel. The reactor barrel was equipped with a steam jacket for even heating of the barrel. The reactor barrel was directly attached to a 15.2 cm×61 cm stainless steel flash tank, oriented vertically. The barrel was isolated from the flash tank by a conical nozzle and seat end shearing valve arrangement. The diameter of the end valve shearing die was 3.5 cm. The backpressure on the conical nozzle and seat was adjustable, with most tests performed using ~138 kPa (gauge pressure) of backpressure into a 10.2 cm diameter air cylinder connected to the cone of the end shear valve. The cone of the end shearing valve could move back up to 1.6 cm to allow discharge of particles in the flash tank. An elbow at the outlet of the end shear valve directed the pretreated solids down into the bottom of the flash tank where the solids were easily removed by unbolting a domed end flange in the bottom of the tank. An upper domed flange to the flash tank incorporated a special outlet fitting with slots machined at right angles to the axis of the flash tank, which caused released vapors to travel around a corner path to an exit fitting, helping to prevent carry-over of entrained biomass particles and water droplets into a vent condenser. Three electrical band heaters (set at 60° C.) and insulation were added along the flash tank to allow hot pretreated solids to flash into a heated vessel, better simulating a commercial scale process.

Steam Gun Reactor Batch Digestion System

The 4-liter steam gun reactor (Autoclave Engineers, Erie, Pa.) is a steam-jacketed reactor consisting of a length of 102 mm schedule 80 Hastelloy® pipe closed by two ball valves. Additional electrical heaters were placed on all exposed, non-jacketed surfaces of the reactor and controlled to the pretreatment set point temperature. Direct steam injection was also used to rapidly bring the biomass up to pretreatment temperature. Steam pressure was adjusted and controlled to maintain the desired pretreatment temperature. The bottom of the reactor was necked down to 51 mm. All pretreated material exited through a replaceable die at the bottom of the reactor and was collected in a nylon (Hotfill®) 0.21 $m^3$ bag supported within a heavy walled, jacketed, and cooled flash tank.

Pretreatment and Enzymatic Hydrolysis Reactor (PEHReactor)

The 9-L PEHReactor (constructed at NREL, Golden, Colo.; see co-pending U.S. patent application Ser. No. 11/402,464) has an approximately 15 cm×51 cm stainless steel reaction vessel and the 3.2-L PEHReactor has a 15 cm×18 cm stainless steel reaction vessel. Each vessel has an injection lance extending through the longitudinal center of the reaction vessel for introduction of processing reactants.

The injection lance is connected using a rotary joint to a port in a cover on one end of the vessel, which has an additional port for vessel access. Four baffles run the length of the vessel wall, and are attached perpendicularly to the wall. The baffles and ceramic attrition media cylinders of 3.2 cm×3.2 cm (E.R. Advanced Ceramics, East Palestine, Ohio), free floating in the vessel, apply mechanical mixing of biomass and reactant as the vessel is rotated, promoting assimilation of reactant into the biomass. Seven cylinders are used in the small reactor and twenty-two in the large reactor. The PEHReactor is placed on a Bellco Cell-Production Roller Apparatus (Bellco Technology, Vineland, N.J.) which provides a mechanism for rotation, and the reactor with roller apparatus is housed in a temperature controlled chamber which provides heat. Vacuum and pressure may be applied to the reaction vessel by attaching external sources to the lance-connected port in the cover.

Fed-batch Saccharification Reactor

The fed-batch saccharification reactor is a 15-L fermentor (B. Braun Biotech International, Allentown, Pa.) controlled by a BioStat ED data control unit and associated control module containing a circulating pump, acid and base pumps, solenoid valves, heat exchangers for temperature control, steam supply, process water, air supply control valves and filtration, and back pressure control valves and exhaust filters. The fermentor was equipped with two 11.4 cm diameter three-blade high efficiency Ligntnin A-310 impellers. The bottom impeller was located 7.6 cm from the reactor bottom (it could not be located any closer due to the presence of a large seal arrangement near the bottom of the shaft for the bottom-drive shaft penetration) and the upper impeller was located 22.9 cm from the reactor bottom. The fermentor vessel has a diameter of 19.0 cm and a maximum height of 55.9 cm. Four removable baffles were installed, each of which has a width of 1.6 cm and a length of 48.3 cm and extended from the vessel bottom to within ~7.6 cm of the top. Plumbed into the top and bottom ports on the fermenter system was a pump-around loop consisting of an APV lobe pump (model M1/028/06), 1-½-in (3.81 cm) flexible hoses and a Teflon sight flow indicator. The pump around loop was isolated from the fermentation vessel with 1-½-in (3.81 cm) Valmicro and SVF full port ball valves with CF8M bodies, 316 s.s. balls, and PTFE seats. Additionally, a V-port shear valve (Triac Controls) was located downstream of the lobe pump, prior to the ball valve isolating the pump from the top port of the fermentor. During the recirculation cycles, this valve was gradually closed to up to 60° to provide greater shearing of the recirculating pretreated solids.

Analytical Methods

Cellulose Quantitation

The amount of cellulose in each starting biomass sample was determined using methods well known in the art, such as ASTM E1758-01 "Standard method for the determination of carbohydrates by HPLC". Measurement of sugar, acetamide, lactic acid and acetic acid content Soluble sugars (glucose, cellobiose, xylose, galactose, arabinose and mannose), acetic acid and ethanol in saccharification liquor or fermentation broth were measured by HPLC (Agilent Model 1100, Agilent Technologies, Palo Alto, Calif.) using Bio-Rad HPX-87P and Bio-Rad HPX-87H columns (Bio-Rad Laboratories, Hercules, Calif.) with appropriate guard columns. The sample pH was measured and adjusted to 5-6 with sulfuric acid if necessary. The sample was then passed through a 0.2 µm syringe filter directly into an HPLC vial. The HPLC run conditions were as follows:

HPX-87P (for carbohydrates):
Injection volume: 10-50 µL, dependent on concentration and detector limits
Mobile phase: HPLC grade water, 0.2 µm filtered and degassed
Flow rate: 0.6 mL/minute
Column temperature: 80-85° C., guard column temperature <60° C.
Detector temperature: as close to main column temperature as possible
Detector: refractive index
Run time: 35 minute data collection plus 15 minute post run (with possible adjustment for later eluting compounds)
Biorad Aminex HPX-87H (for carbohydrates, acetic acid and ethanol)
Injection volume: 5-10 µL, dependent on concentration and detector limits
Mobile phase: 0.01N Sulfuric acid, 0.2 µm filtered and degassed
Flow rate: 0.6 mL/minute
Column temperature: 55° C.
Detector temperature: as close to column temperature as possible
Detector: refractive index
Run time: 25-75 minute data collection After the run, concentrations in the sample were determined from standard curves for each of the compounds.

Example 1

Pretreatment of Cob in the Small Barrel Piston Reactor

Whole corn cobs were processed with a jaw crusher (2.2 kW motor) with a jaw spacing of approximately 0.95 cm, followed by a delumper (1.5 kW motor, Franklin Miller Inc., Livingston, N.J.), followed by screening with a Sweco screen equipped with a 1.9 cm U.S. Standard screen to fracture the whole cobs into smaller pieces. The small barrel piston reactor (described in General Methods) was charged with 115 g (dry weight basis) fractured cobs, by hand placing of cobs into the end of the reactor with the piston removed. The piston was replaced to plug the end. A vacuum was applied to the reactor vessel to bring the reactor pressure to <10 kPa (0.1 bar), and dilute ammonium hydroxide solution was injected to give an ammonia concentration of either 4 g or 6 g per 100 g dry weight of biomass (as given in Table 1) and a dry weight of biomass concentration of 50 g per 100 g total biomass-aqueous ammonia mixture. After the ammonia solution was charged, steam was injected to bring the temperature to 145° C. inside the reactor. The biomass was held at temperature for 20 minutes and then discharged into the flash tank by activating the piston. During the 20 minute pretreatment, temperature was monitored and steam was added as necessary to maintain temperature. Pretreated cobs were harvested through the bottom of the flash tank. Excess free liquid was removed and remaining solids were used in saccharification.

For saccharification, about 470 g of pretreated biomass was added to the 3.2-L PEHR reactor described in General Methods. The pH of the contents was adjusted to approximately 5.5 by injecting 1 M citric acid buffer at pH 4.8 plus adding citric acid monohydrate. Once the desired pH was reached, 12.9 mg/g cellulose or 25.8 mg/g cellulose of Spezyme® CP cellulase (Genencor International, Rochester, N.Y.) and 4.2 mg active protein/g cellulose or 8.4 mg active protein/g cellulose of hemicellulase enzyme consortium (Diversa; San Diego, Calif.) consisting of β-glucosidase, xylanase, β-xylosidase and arabinofuranosidase were loaded into the reactor. Buffer, enzymes and water were added such that the final mixture in the reactor consisted of 23 g dry biomass/100 g pretreated biomass-saccharification enzyme consortium mixture. The reactor remained in an incubator at 50° C. rolling at 19 rpm for 72 hr. Yields given in Table 1 below are the release as percent of theoretical yield.

TABLE 1

Yields following saccharification of cob pretreated in the small barrel piston reactor.

| Ammonia (g/100 g DWB) | Spezyme ® CP (mg/g cellulose) | Enzyme consortium (Diversa) (mg/g cellulose) | Monomer Glucose Release (% theoret) | Total Glucose Release (% theoret) | Monomer Xylose Release (% theoret) | Total Xylose Release (% theoret) |
|---|---|---|---|---|---|---|
| 4 | 25.8 | 8.4 | 78 | 90 | 50 | 80 |
| 6 | 12.9 | 4.2 | 65 | 77 | 48 | 72 |

Example 2

Pretreatment in the Large Barrel Piston Reactor at Different Times

Steam was added to the jacket of the barrel to preheat the barrel of the large barrel piston reactor (described in General Methods) to ~130° C. The flash receiver was preheated to ~60° C. with band heaters. Fractured cobs were prepared as described in Example 1. These cobs (175 g, dry weight basis) were loaded into the large barrel reactor, by hand placing of cobs into the end of the reactor with the piston removed. The piston was replaced to plug the end. A vacuum was applied to the reactor vessel and to the flash receiver to bring the pressure down <10 kPa, and dilute ammonium hydroxide solution was injected into the reactor to give an ammonia concentration of 6 g/100 g dry weight of biomass and a dry weight of biomass concentration of 45 g/100 g total biomass-aqueous ammonia mixture. Once the ammonia was charged, steam was injected into the reactor to bring the temperature to 145° C. The mixture was held at this temperature for 10 or 20 minutes by monitoring the temperature and adding steam as necessary and then discharged into the preheated flash tank by activating the piston. Vacuum was pulled on the flash tank until the flash receiver reached ~59° C. Three 10 minute pretreatments and six 20 minute pretreatments were carried out, with all material pretreated for the same length of time pooled at the end. Upon harvest from the flash receiver, free liquid was separated from the pretreated solids and not added back for saccharification. A sample of the pretreated cob was subsequently saccharified as described in Example 1 in the small PEHReactor. All saccharifications were done with 12.9 mg/g cellulose of Spezyme® CP cellulase and 4.2 mg active protein/g cellulose of hemicellulase enzyme consortium (Diversa) containing xylanase, β-xylosidase, arabinofuranosidase and β-glucosidase at 50° C. and pH 5.5 for 72 hr. Yields given in Table 2 below are the release as percent of theoretical yield.

TABLE 2

Yields following saccharification of cob pretreated in the large barrel piston reactor.

| Pretreatment time (min) | Monomer Glucose Release (% theoret) | Total Glucose Release (% theoret) | Monomer Xylose Release (% theoret) | Total Xylose Release (% theoret) |
|---|---|---|---|---|
| 10 | 68.2 | 79.5 | 32.1 | 77.0 |
| 20 | 68.0 | 83.2 | 39.1 | 84.3 |

Example 3

Pretreatment in Large Barrel Piston Reactor Compared to Steam Gun

Size-reduced cobs were prepared as described in Example 1. Pretreatment in the large barrel piston reactor was carried out as described in Example 2. For pretreatment in the steam gun, cobs were first loaded into a 9-L PEHReactor. The reactor was cooled to 4° C. by rotation in contact with ice on the outer surface. A vacuum was applied to the vessel, and dilute ammonium hydroxide solution that was pre-cooled in a cold room at 4° C. and passed through tubing immersed in an ice-water bath was injected to give an ammonia concentration of 6 g/100 g dry weight of biomass and a dry weight of biomass concentration of 45 g/100 g total biomass-aqueous ammonia mixture. The PEHReactor charged with ammonia and cob was cooled to 4° C. by applying ice to the surface of the rotating reactor vessel and rotated at 4° C. for 30 min. At this time the contents were transferred to the steam gun reactor that is described in General Methods. Once the steam gun reactor was charged with the ammonia-cob mixture, the temperature was increased to 145° C. by direct injection of steam. The cob-ammonia mixture was held at this temperature for 20 min, and then the mixture was discharged into a flash tank.

Samples of pretreated cob were taken from both the large barrel piston reactor and steam gun reactor, and saccharified as described in Example 1. Saccharifications were carried out with 12.9 mg/g cellulose Spezyme® CP cellulase (Genencor) and 4.2 mg active protein/g cellulose of hemicellulase enzyme consortium (Diversa) consisting of β-glucosidase, xylanase, β-xylosidase and arabinofuranosidase. The reactor remained in the incubator at 50° C. and 19 rpm for 72 hr. Resulting glucose yields for pretreatment in each reactor are shown in Table 3 below.

TABLE 3

Yields following saccharification of cobs pretreated in either the large barrel piston reactor or steam gun.

| Pretreatment reactor | DWB conc in reactor | Pretreatment time (min) | Pretreatment temperature (° C.) | Monomer Glucose Release (% theoret) | Total Glucose Release (% theoret) | Monomer Xylose Release (% theoret) | Total Xylose Release (% theoret) |
|---|---|---|---|---|---|---|---|
| piston reactor | 50% | 20 | 145 | 68.0 | 83.2 | 39.1 | 84.3 |
| Steam gun | 60% | 40 | 150 | 65 | 77 | 48 | 82 |

Example 4

Pretreatment of Corn Cob and Fiber Blends in Large Barrel Piston Reactor

Fractured corn cobs were prepared as described in Example 1. Fractured cobs alone and fractured cobs blended with Cargill Bran 80 (Cargill, Minnetonka, Minn.) were pretreated in the large barrel piston reactor. Fractured cobs and Cargill Bran 80 corn fiber were combined such that the fiber was approximately 33% of the total dry biomass of the mixed sample. In each case 175 g (dry weight basis) feedstock was added to the reactor. Pretreatment was carried out essentially as described in Example 2. However, in these experiments, after addition of ammonia solution, the reactor contents were held for 10 min before injecting steam to bring the temperature to 145° C. After steam injection, temperature was held for 10 min at 145° C. by adding steam when necessary. Following the pretreatment, the sample was discharged into a flash tank with activation of the piston.

Samples of the pretreated cob and cob-fiber blend were taken from the flash tank of the large barrel piston reactor and saccharified in small PEHReactors as described in Example 1. Biomass was added such that 20% of the reactor volume was filled. Saccharifications were carried out with 12.9 mg/g cellulose of Spezyme® CP cellulase (Genencor) and 15 mg/g cellulose of Multifect xylanase (Genencor). The PEHReactors remained in the incubator at 50° C. and 19 rpm for 72 hr. Resulting glucose and xylose yields for pretreatment are shown in Table 4 below.

TABLE 4

Yields following saccharification of cob and cob/bran samples pretreated in the large barrel piston reactor.

| Feedstock | DWB conc in reactor | Monomer Glucose Release (% theoret) | Total Glucose Release (% theoret) | Monomer Xylose Release (% theoret) | Total Xylose Release (% theoret) |
|---|---|---|---|---|---|
| Cob only | 45% | 40.2 | 67.2 | 29.4 | 83.9 |
| Cob + bran 80 | 45% | 37.0 | 65.4 | 21.6 | 77.2 |

Example 5

Production of Ethanol from Corn Cobs Pretreated in the Large Barrel Piston Reactor Pretreatment of corn cobs was carried out for 10 minutes as described in Example 2. A total of 17 such pretreatments were carried out. Pretreated cobs from 4 pretreatments were pooled for saccharification to provide initial hydrolysate for the fed-batch saccharification. Pretreated cobs from the remaining 13 runs were pooled for use in the fed-batch saccharification.

To start the fed-batch saccharification, the fed-batch saccharification reactor described in General Methods was first loaded with hydrolysate to fill the reactor volume up to the bottom of the first impeller. This hydrolyzate was prepared by saccharifying pretreated cobs in 2.8-L shake flasks. These shake flasks were loaded with 465 g pretreated solids, 1000 ml DI water, and enzymes at 28.4 mg Spezyme® CP/g cellulose and 4.2 mg active protein/g cellulose hemicellulase enzyme consortium (Diversa) comprising β-glucosidase, xylanase, β-xylosidase and arabinofuranosidase. Prior to enzyme addition, pH was adjusted to 5 with 8.5% $H_3PO_4$. The shake flasks were maintained at 50° C. and 150 rpm in a rotary shaker for 48 hr, at which time the hydrolysate was loaded into the fed-batch reactor.

Once the initial hydrolysate was loaded, the first aliquot of the pretreated biomass-ammonia mixture (~700 g) was added to the reactor. The pH was maintained at a setpoint of 5.5 by addition of 8.5% $H_3PO_4$. Once the pH readjusted to the setpoint, 28.4 mg of Spezyme® CP/g cellulose and 4.2 mg active protein/g cellulose of hemicellulase enzyme consortium (Diversa) comprising β-glucosidase, xylanase, β-xylosidase and arabinofuranosidase were added. Additional aliquots of the pretreated biomass-ammonia mixture, Spezyme® CP cellulase and hemicellulase enzyme consortium were added at t=4, 8, 12, 22, 26, 30 and 34 hr. The pump around loop was generally started about 1 hr after enzyme addition and was run for about 1 hr up through the 22 hr solids addition. After the 26 hr and 30 hr additions, the pump was started about 50 min after enzyme addition and run for 30 minutes. After the 34 hr addition, the pump was started ~3 hr after enzyme addition and run for 30 minutes. The pump was also run for 30 minutes at t=29, 33, 47 and 49 hr. Total saccharification time was 120 hr. At this time, hydrolysate contained ~60 g/L monomer glucose, 25 g/L monomer xylose and 10 g/L acetic acid.

This hydrolyzate was used for fermentation of *Zymomonas mobilis* strains ZW800 or ZW658 (ATCC # PTA-7858). ZW658 is a strain of *Zymomonas mobilis* that has been engineered for xylose fermentation to ethanol and is described in co-owned and co-pending U.S. Patent Application 60/847,813, which is herein incorporated by reference. ZW658 was constructed by integrating two operons, $P_{gap}$xylAB and $P_{gap}$taltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. ZW800 is the ZW658 strain with the gene encoding glucose-fructose oxidoreductase inactivated, which is also described in co-owned and co-pending U.S. Patent Application 60/847,813.

Fermentations were carried out in sterilized 1-liter fermentors (BIOSTAT® B-DCU system, Sartorius BBI System Inc., Bethlehem, Pa., USA) with 500 ml initial working volume. Inoculum was added to the fermentor at a level of 10% (v/v) such that the $OD_{600}$~1 in the broth after addition. Hydrolysate was present at 80% or 40% (v/v), with the balance as water. Additional glucose and xylose were added to bring final concentrations in the broth to 92 g/L and 82 g/L, respectively. Broth was also supplemented with 10 mM sorbitol and 1 g/L $MgSO_4.7H_2O$. Fermentation was carried out for 72 hr at 33° C., pH 5.8 with 150 rpm agitation. Final ethanol titers for the ZW800 strain were 8 g/L in the 40% hydrolysate and 7 g/L in the 80% hydrolysate. For ZW658, the final ethanol titers were 8 g/L in 40% hydrolyzate and 6.5 g/L in 80% hydrolyzate.

What is claimed is:

1. A method for treating biomass comprising:
   a) providing biomass;
   b) loading the biomass of (a) using a non-compacting feeder into an apparatus comprising;
      i) a cylindrical barrel having a first end fitted with a piston and a second end fitted with a discharge valve;
      ii) optionally, an offset attached at one offset end to the cylindrical barrel near the cylindrical barrel first end, and having a sealable valve at the unattached offset end;
      iii) at least 2 sealable ports in the cylindrical barrel or in the offset;
      iv) optionally, a valve in the cylindrical barrel dividing the barrel into separate first and second chambers, said first chamber having the barrel first end fitted with said piston, and said second chamber having the barrel second end with the discharge valve; and
      v) a flash tank attached to the discharge valve at the second end of the barrel;
   wherein said biomass is loaded into the cylindrical barrel or optionally into said offset attached to said cylindrical barrel;
   c) closing off said cylindrical barrel and offset, if present;
   d) optionally applying vacuum via at least one port in the cylindrical barrel;
   e) adding through said at least one port in the cylindrical barrel or offset an aqueous solution comprising ammonia in an amount that is less than about 12 weight percent relative to dry weight of biomass in the barrel, creating a biomass and aqueous ammonia mixture, and further wherein the dry weight of biomass is at a high solids concentration of at least about 15 weight percent relative to the weight of the biomass and aqueous ammonia mixture, and adding steam through said second port in the cylindrical barrel or offset, if present, to reach a temperature inside the barrel that is between about 85° C. and about 180° C.;
   f) closing the ports in the cylindrical barrel and offset, if present, to provide an impermeable chamber;
   g) holding the biomass and aqueous ammonia mixture in the impermeable chamber at a suitable temperature that is between about 85° C. and about 180° C. for a time that is between about 30 seconds and about 4 hours;
   h) optionally moving the biomass and aqueous ammonia mixture to a second chamber in the cylindrical barrel, if present, by displacement with said piston wherein the biomass is not compacted, and holding it for a time that is between about 2 minutes and 4 hours; and
   i) moving the biomass and aqueous ammonia mixture with said piston through the impermeable chamber of (g) or second chamber of (h) through the discharge valve into the flash tank;
   wherein treated biomass is produced.

2. The method of claim 1 wherein one or more of steps (a), (b), (c), (d), (e), (f), (g), and (h) are repeated at least once prior to (i).

3. A method for treating biomass comprising:
   a) providing a mixture of biomass and an aqueous solution comprising ammonia wherein the dry weight of biomass is at least about 15 weight percent relative to total weight of the biomass and aqueous ammonia mixture, and the aqueous ammonia is in an amount that is less than about 12 weight percent relative to dry weight of biomass;
   b) loading the biomass and aqueous ammonia mixture of (a) using a non-compacting feeder into an apparatus comprising;
      i) a cylindrical barrel having a first end fitted with a piston and a second end fitted with a discharge valve;
      ii) optionally, an offset attached at one offset end to the cylindrical barrel near the cylindrical barrel first end, and having a sealable valve at the unattached offset end;
      iii) at least 2 sealable ports in the cylindrical barrel or in the offset;
      iv) a valve in the cylindrical barrel dividing the barrel into separate first and second chambers, said first chamber having the barrel first end fitted with said piston, and said second chamber having the barrel second end with the discharge valve; and
      v) a flash tank attached to the discharge valve at the second end of the barrel;
   wherein said biomass is loaded into the first chamber of the cylindrical barrel or optionally into said offset attached to said cylindrical barrel;
   c) closing off said first chamber in the barrel and the offset, if present;
   d) optionally applying vacuum via said least one port;
   e) adding through the least one first port in the first chamber or offset, if present, steam to reach a temperature inside the chamber that is between about 85° C. and about 180° C.;
   f) closing the ports in the first chamber and offset, if present, to provide an impermeable first chamber;
   g) holding the biomass and aqueous ammonia mixture in the impermeable first chamber at a suitable temperature that is between about 85 ° C. and about 180 ° C. for a time that is between about 30 seconds and about 4 hours;
   h) optionally, moving the biomass and aqueous ammonia mixture through an opened valve into the second chamber of the cylindrical barrel by displacement with a piston through the impermeable first chamber wherein the biomass is not compacted, i) optionally, closing the opened valve to form a second impermeable chamber and holding the biomass and aqueous ammonia mixture for a time that is between about 2 minutes and about 4 hours; and j) moving the biomass and aqueous ammonia mixture by displacement with a piston following step (g) or step (i) through the discharge valve into the flash tank;

wherein the biomass is not compacted and whereby treated biomass is produced.

4. The method of claim 3 wherein one or more of steps (a), (b), (c), (d), (e), (f), (g), (h) and (i) are repeated at least once prior to (j).

5. The method of claim 1 or 3 wherein no de-compaction step is included.

6. The method of claim 1 or 3 wherein the aqueous ammonia is between about 4% and about 6% relative to dry weight of biomass.

7. The method of claim 1 or 3 wherein the dry weight of biomass is at least about 20% relative to the weight of the biomass and aqueous ammonia mixture.

8. The method of claim 7 wherein the dry weight of biomass is at least about 30% relative to the weight of the biomass and aqueous ammonia mixture.

9. The method of claim 8 wherein the dry weight of biomass is at least about 50% relative to the weight of the biomass and aqueous ammonia mixture.

10. The method of claim 1 or 3 wherein the suitable temperature is between about 120° C. and about 160° C.

11. The method of claim 10 wherein the suitable temperature is between about 140° C. and about 150° C.

12. The method of claim 1 or 3 wherein the non-compacting feeder of (b) is a hopper equipped with a non-compacting flow inducer.

13. The method of claim 1 or 3 wherein the first cylindrical chamber is closed with at least one valve.

14. The method of claim 13 wherein the first chamber is closed with a first valve to close off the non-compacting feeder and a second valve to close off the second chamber of (h).

15. The method of claim 1 or 3 wherein the discharge valve is a gradual expansion venturi.

16. The method of claim 1 or 3 wherein said biomass is selected from the group consisting of switchgrass, waste paper, sludge from paper manufacture, corn grain, corn cobs, corn husks, corn fiber, corn stover, grasses, wheat, wheat straw, hay, barley, barley straw, rice straw, sugar cane bagasse, sorghum, soy, components obtained from milling of grains, trees, branches, roots, leaves, wood chips, sawdust, shrubs and bushes, vegetables, fruits, flowers and animal manure.

17. The method of claim 16 wherein biomass is selected from the group consisting of corn cobs, corn stover, corn fiber, corn husks, sugar cane bagasse, sawdust, switchgrass, wheat straw, hay, rice straw, and grasses.

18. The method of claim 17 wherein biomass is selected from the group consisting of corn cobs, corn stover, corn fiber, sawdust, and sugar cane bagasse.

19. The method of claim 1 or 3 wherein said biomass is derived from multiple feedstocks.

* * * * *